US011584724B2

(12) United States Patent
Maloney et al.

(10) Patent No.: US 11,584,724 B2
(45) Date of Patent: Feb. 21, 2023

(54) PROCESS FOR SYNTHESIS OF A PHENOXY DIAMINOPYRIMIDINE COMPOUND

(71) Applicants: Merck Sharp & Dohme Corp., Rahway, NJ (US); Werthenstein BioPharma GmbH, Werthenstein (CH)

(72) Inventors: Kevin M. Maloney, Metuchen, NJ (US); Kallol Basu, Hillsborough, NJ (US); Michael James Di Maso, Hamilton, NJ (US); Guy R. Humphrey, Hillsborough, NJ (US); Alfred Y. Lee, Robbinsville, NJ (US); Feng Peng, Dayton, NJ (US); Hong Ren, Green Brook, NJ (US); Siwei Zhang, Westfield, NJ (US)

(73) Assignees: Merck Sharp & Dohme LLC, Rahway, NJ (US); Werthenstein BioPharma GmbH, Werthenstein (CH)

(*) Notice: Subject to any disclaimer, the term of this patent is extended or adjusted under 35 U.S.C. 154(b) by 10 days.

(21) Appl. No.: 17/048,833

(22) PCT Filed: Apr. 18, 2019

(86) PCT No.: PCT/US2019/028014
§ 371 (c)(1),
(2) Date: Oct. 19, 2020

(87) PCT Pub. No.: WO2019/209607
PCT Pub. Date: Oct. 31, 2019

(65) Prior Publication Data
US 2021/0122717 A1  Apr. 29, 2021

Related U.S. Application Data

(60) Provisional application No. 62/662,991, filed on Apr. 26, 2018, provisional application No. 62/661,362, filed on Apr. 23, 2018.

(51) Int. Cl.
*C07D 239/48* (2006.01)
*C07C 41/09* (2006.01)
*C07C 41/30* (2006.01)
*C07C 253/30* (2006.01)
*C07D 487/18* (2006.01)

(52) U.S. Cl.
CPC ......... *C07D 239/48* (2013.01); *C07C 41/09* (2013.01); *C07C 41/30* (2013.01); *C07C 253/30* (2013.01); *C07D 487/18* (2013.01); *C07B 2200/13* (2013.01)

(58) Field of Classification Search
CPC .................................................. C07D 239/48
See application file for complete search history.

(56) References Cited

U.S. PATENT DOCUMENTS

| 4,422,955 A | 12/1983 | Bryant |
| 7,741,484 B2 | 6/2010 | Constantinescu et al. |
| 9,643,934 B2 | 5/2017 | Dvorak et al. |
| 2009/0042964 A1 | 2/2009 | Malamas et al. |
| 2017/0326142 A1 | 11/2017 | Ford et al. |

FOREIGN PATENT DOCUMENTS

| WO | 2008040652 A1 | 4/2008 |
| WO | 2018118668 A1 | 6/2018 |

OTHER PUBLICATIONS

Ren, Hong, et al. "Development of a Green and Sustainable Manufacturing Process for Gefapixant Citrate (MK-7264) Part 1: Introduction and Process Overview." Org. Process Res. Dev. (2020), vol. 24, pp. 2445-2452. (Year: 2020).*
Caira, Crystalline Polymorphism of organic compounds, Topics in Current Chemistry, 1998, 163-208, 198.
Guo, Wen-Sheng et al., Cocrystal Phenomena of DABCO with Phenol Derivatives, Chemical Research in Chinese Universities, 1993, 261-263, 9 (3).
Takahashi, Naoki et al., Synthesis and pharmacological characterization of 1-benzyl-4-aminoindole-based thyroid hormone receptor beta agonists, Bioorganic & Medicinal Chemistry, 2014, 488-498, 22 (1).
Dabros, Marta, A Supramolecular Approach to Organic Alloys: Cocrystals and Three- and Four-Component Solid Solutions of 1,4-Diazabicyclo[2.2.2]octane and 4-X-Phenols (X=Cl, CH3, Br), Angewandte Chemie International Edition, 2007, 4132-1135, 46.
Werry, Brian Scott, Modifiable Poly(arylene ether)s and Hyperbranched Poly(esters), Wright State University, 2007, 1-82, Core Scholar.
Node, Manabu et al., Efficient Asymmetric Synthesis of abeo-Abietane-Type Diterpenoids by Using the Intramolecular Heck Reaction, J. Org. Chem., 2010, 190-196, 75.

* cited by examiner

*Primary Examiner* — John S Kenyon
(74) *Attorney, Agent, or Firm* — Julie M. Lake; Catherine D. Fitch

(57) ABSTRACT

Disclosed herein is a novel process for preparing Compound A free base, 5-((2,4-diaminopyrimidin-5-yl)oxy)-4-iso-propyl-2-methoxybenzenesulfonamide, and a citrate salt of Compound A with simplified chemistry and a high overall yield: Compound A. In one embodiment, the overall yield from the starting material 2-isopropylphenol to Compound A citrate salt is greater than 50%. In another embodiment, the overall yield is greater than 60%. Also disclosed herein are novel salts and solvates of Compound A.

20 Claims, 6 Drawing Sheets

An XRPD pattern of 4-bromo-2-isopropylphenol hemi-DABCO co-crystal

An XRPD pattern of 4-bromo-2-isopropylphenol mono-DABCO co-crystal

An XRPD pattern of Compound A free base acetonitrile solvate 1

An XRPD pattern of Compound A citrate methanol solvate 1

PROCESS FOR SYNTHESIS OF A PHENOXY DIAMINOPYRIMIDINE COMPOUND

CROSS REFERENCE TO RELATED APPLICATIONS

The present application is the 371 national phase application of International Application No. PCT/US2019/028014, filed Apr. 18, 2019, which claims the benefit of U.S. Provisional Application Nos. 62/661,362, filed Apr. 23, 2018, and 62/662,991, filed Apr. 26, 2018, hereby incorporated by reference in their entirety.

FIELD OF THE INVENTION

The present invention is directed to a novel process for preparing a phenoxy diaminopyrimidine compound, or a pharmaceutically acceptable salt thereof, which is useful for the potential treatment of diseases associated with P2X purinergic receptors, for example, respiratory and pain-related diseases, conditions and disorders.

BACKGROUND OF THE INVENTION

P2X receptor subunits are found on afferents in rodent and human bladder urothelium. Data exists suggesting that ATP may be released from epithelial/endothelial cells of the urinary bladder or other hollow organs as a result of distention (Burnstock (1999) J. Anatomy 194:335-342; and Ferguson et al. (1997) J. Physiol. 505:503-511). ATP released in this manner may serve a role in conveying information to sensory neurons located in subepithelial components, e.g., suburothelial lamina propria (Namasivayam, et al. (1999) BJU Intl. 84:854-860). The P2X receptors have been studied in a number of neurons, including sensory, sympathetic, parasympathetic, mesenteric, and central neurons (Zhong, et al. (1998) Br. J. Pharmacol. 125:771-781). These studies indicate that purinergic receptors may play a role in afferent neurotransmission from the bladder, and that modulators of P2X receptors are potentially useful in the treatment of bladder disorders and other genitourinary diseases or conditions.

Recent evidence also suggests a role of endogenous ATP and purinergic receptors in nociceptive responses in mice (Tsuda, et al. (1999) Br. J. Pharmacol. 128:1497-1504). ATP-induced activation of P2X receptors on dorsal root ganglion nerve terminals in the spinal cord has been shown to stimulate release of glutamate, a key neurotransmitter involved in nociceptive signaling (Gu and MacDermott, Nature 389:749-753 (1997)). P2X3 receptors have been identified on nociceptive neurons in the tooth pulp (Cook et al., Nature 387:505-508 (1997)). ATP released from damaged cells may thus lead to pain by activating P2X3 and/or P2X2/3 containing receptors on nociceptive sensory nerve endings. This is consistent with the induction of pain by intradermally applied ATP in the human blister-base model (Bleehen, Br J Pharmacol 62:573-577 (1978)). P2X antagonists have been shown to be analgesic in animal models (Driessen and Starke, Naunyn Schmiedebergs Arch Pharmacol 350:618-625 (1994)). This evidence suggests that P2X2 and P2X3 are involved in nociception, and that modulators of P2X receptors are potentially useful as analgesics.

Other researchers have shown that P2X3 receptors are expressed in human colon, and are expressed at higher levels in inflamed colon than in normal colon (Y. Yiangou et al, Neuroeastroenterol Mot (2001) 13:365-69). Other researchers have implicated the P2X3 receptor in detection of distension or intraluminal pressure in the intestine, and initiation of reflex contractions (X. Bian et al., J Physiol (2003) 551.1:309-22), and have linked this to colitis (G. Wynn et al., Am J Physiol Gastrointest Liver Physiol (2004) 287:G647-57); Inge Brouns et al. (Am J Respir Cell Mol Biol (2000) 23:52-61) found that P2X3 receptors are expressed in pulmonary neuroepithelial bodies (NEBs), implicating the receptor in pain transmission in the lung. Researchers have also implicated P2X2 and P2X3 receptors in pO2 detection in pulmonary NEBs (W. Rong et al., J Neurosci (2003) 23(36):11315-21).

There is accordingly a need for improved methods of making compounds that are effective modulators of P2X receptors, including the P2X3 and P2X2/3 receptors.

U.S. Pat. Nos. 7,858,632 and 7,741,484 disclose methodology and synthetic routes that can be used to prepare phenoxy diaminopyrimidine derivatives. However, the currently known methods have various drawbacks including complex chemistry and/or lower yield. There remains a need for improved synthetic methods for preparing phenoxy diaminopyrimidine derivatives with simplified chemistry and/or a higher yield.

SUMMARY OF THE INVENTION

Disclosed herein is a novel process for preparing Compound A, a phenoxy diaminopyrimidine compound of the following formula, or a pharmaceutically acceptable salt thereof:

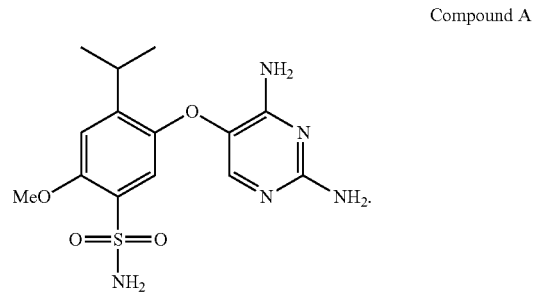 [SMILES: COc1cc(C(C)C)c(Oc2cnc(N)nc2N)cc1S(N)(=O)=O]

Compound A

Also disclosed herein are various salts and solvates of Compound A.

DETAILED DESCRIPTION OF THE INVENTION

Figure 1:
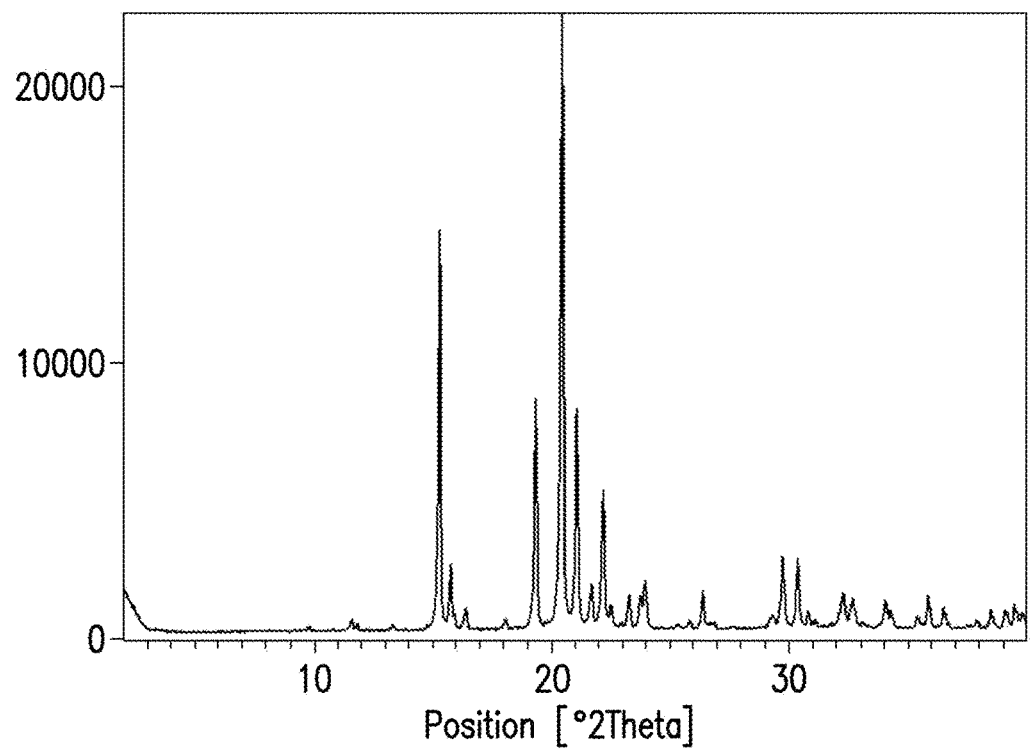
FIG. 1. An XRPD pattern of 4-bromo-2-isopropylphenol hemi-DABCO co-crystal.

A process for preparing Compound A free base, or a pharmaceutically acceptable salt thereof, with simplified chemistry and higher yield is disclosed herein.

In one embodiment, the citrate salt of Compound A is obtained by a process comprising synthesis and isolation of a 4-bromo-2-isopropylphenol DABCO co-crystal, synthesis of 2-isopropyl-4-methoxyphenol and 2-(2-isopropyl-4-methoxyphenoxy)acetonitrile, synthesis and isolation of 5-(2-isopropyl-4-methoxyphenoxy)pyrimidine-2,4-diamine, synthesis of Compound A free base, 5-((2,4-diaminopyrimidin-5-yl)oxy)-4-isopropyl-2-methoxybenzenesulfonamide, and final conversion of Compound A free base to a corresponding citrate salt, as shown in Scheme 1.

In one embodiment, the 4-bromo-2-isopropylphenol DABCO co-crystal is converted to 2-isopropyl-4-methoxyphenol in the presence of copper (I) bromide, DMF, and sodium methoxide. In one embodiment, DMF and DABCO are both required in this reaction to prevent dimerization of the product.

In an alternative embodiment, the 2-isopropyl-4-methoxyphenol is synthesized from mequinol in the presence of dirhenium decarbonyl and propylene at high temperatures and pressures.

In one embodiment, the 2-isopropyl-4-methoxyphenol is treated with an alkylating agent to provide the desired 2-(2-isopropyl-4-methoxyphenoxy)acetonitrile. In one embodiment, this reaction is run with potassium carbonate in acetonitrile. In another embodiment, this reaction is run with sodium hydroxide in a mixture of toluene and NMP. These reaction conditions allow for the complete conversion of the phenol to 2-(2-isopropyl-4-methoxyphenoxy)acetonitrile, whereas previous methods were unable to effect complete conversion of phenol to 2-(2-isopropyl-4-methoxyphenoxy)acetonitrile.

In one embodiment, 2-(2-isopropyl-4-methoxyphenoxy)acetonitrile is treated with ethyl formate in NMP, and this

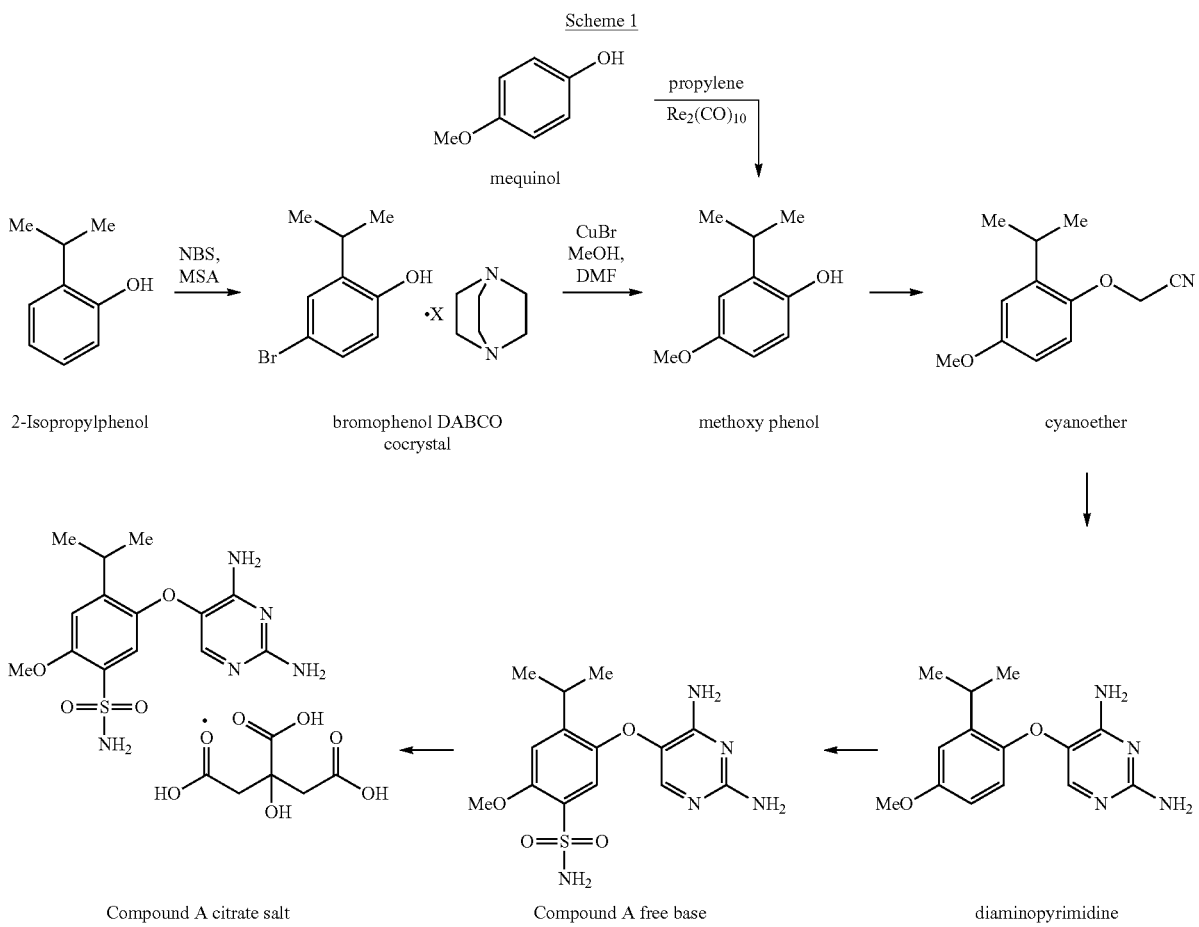

Scheme 1

In one embodiment, 2-isopropylphenol is treated with NBS in the presence of MSA to form 4-bromo-2-isopropylphenol. This compound is treated with DABCO to produce a solid co-crystal of 4-bromo-2-isopropylphenol with DABCO.

mixture is added to a solution of potassium tert-butoxide in NMP. This order of addition allows for the desired bond to form; whereas addition of reactants in alternative orders may lead to dimerization of the cyanomethyl ether starting material and the generation of carbon monoxide. The resulting enolate is treated with guanidine to provide the 5-(2-isopropyl-4-methoxyphenoxy)pyrimidine-2,4-diamine.

In one embodiment, the 5-(2-isopropyl-4-methoxyphenoxy)pyrimidine-2,4-diamine is treated with chlorosulfonic acid in the presence of acetonitrile to form a sulfonyl chloride intermediate. In acetonitrile, this reaction is homogeneous and can be directly quenched into aqueous ammonium hydroxide to provide the free base of Compound A, 5-((2,4-diaminopyrimidin-5-yl)oxy)-4-isopropyl-2-methoxybenzenesulfonamide.

In one embodiment, the free base Compound A, 5-((2,4-diaminopyrimidin-5-yl)oxy)-4-isopropyl-2-methoxybenzenesulfonamide, is treated with glycolic acid in methanol to form the glycolate salt. Addition of citric acid converts the glycolate salt to the citrate salt in a mixture of methanol and isopropanol to yield Compound A citrate salt. This novel salt metathesis approach to isolation allows for desirable form and impurity control.

The procedure of Scheme 1 provides several important advantages. The synthesis of the 2-isopropyl-5-methoxyphenol intermediate is completed in one or two steps instead of the multiple step sequence required in previous syntheses. The desired alkylation is performed in a safe, controlled manner with no extreme exotherms. The 5-(2-isopropyl-4-methoxyphenoxy)pyrimidine-2,4-diamine is synthesized directly from 2-(2-isopropyl-4-methoxyphenoxy)acetonitrile without any intermediates or isolations, and without the use of anilines which can complicate purification of the desired compound. The chlorosulfonylation reaction is performed in acetonitrile to directly provide the sulfonyl chloride without the need for phosphorous oxychloride. The free base 5-((2,4-diaminopyrimidin-5-yl)oxy)-4-isopropyl-2-methoxybenzenesulfonamide is isolated from a mixture of water and acetonitrile that allows for facile crystallization of several forms of the desired product. This process provides simplified chemistry, a higher yield and utilizes standard manufacturing equipment, thereby affording a productive, environmentally friendly, and portable manufacturing process.

In one embodiment, the instant process comprises a step of converting 2-isopropylphenol to a 4-bromo-2-isopropylphenol DABCO co-crystal:

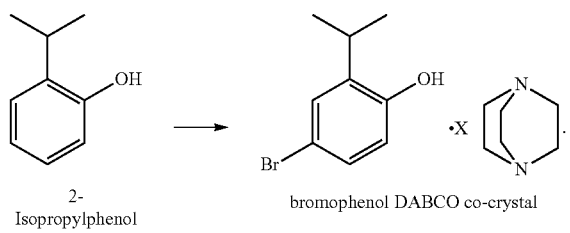

In one embodiment, the above conversion is carried out in the presence of NBS, MSA and a solvent such as MeCN. In another embodiment, hydrogen peroxide and hydrobromic acid can be used. In another embodiment, pyridinium tribromide is used. In another embodiment, other brominating reagents can be used.

In one embodiment, the above conversion is carried out at a temperature of about −5° C. to 10° C., or more specifically about −5° C. to 0° C.

In one embodiment, the 4-bromo-2-isopropylphenol DABCO co-crystal is isolated as the 4-bromo-2-isopropylphenol hemi-DABCO co-crystal. In another embodiment, the co-crystal is isolated as the 4-bromo-2-isopropylphenol mono-DABCO co-crystal.

In one embodiment, a process for preparing 4-bromo-2-isopropylphenol hemi-DABCO co-crystal comprises the following step:

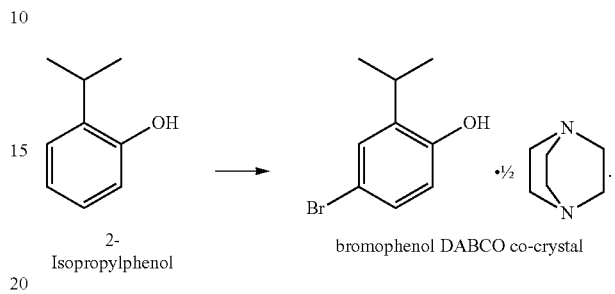

In one embodiment, the instant process further comprises a step of reacting the 4-bromo-2-isopropylphenol DABCO co-crystal with NaOMe to form 2-isopropyl-4-methoxyphenol:

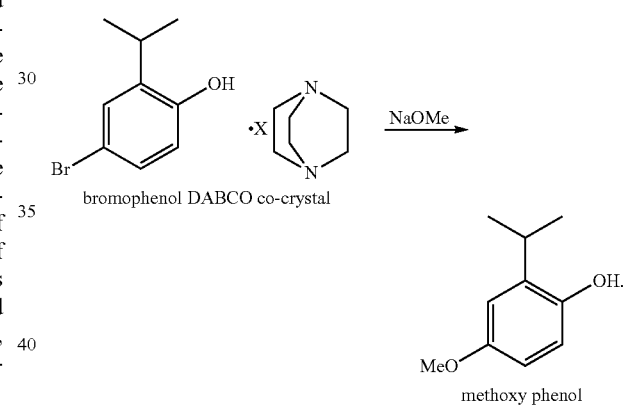

In one embodiment, the above reaction is carried out in the presence of copper (I) bromide as a catalyst. In other embodiments, copper (II) bromide, copper (I) iodide, and other copper (I) or copper (II) salts can be used as a catalyst.

In one embodiment, the 4-bromo-2-isopropylphenol DABCO co-crystal is charged as the 4-bromo-2-isopropylphenol hemi-DABCO co-crystal. In another embodiment, the co-crystal is charged as the 4-bromo-2-isopropylphenol mono-DABCO co-crystal.

In one embodiment, the reaction is carried out in the presence of MeOH and DMF. In other embodiments, dimethylacetamide, dioxane, or DMSO can be used as a solvent.

In one embodiment, the 2-isopropyl-4-methoxyphenol is not isolated. In another embodiment, the 2-isopropyl-4-methoxyphenol is isolated as an anhydrate. In a further embodiment, the 2-isopropyl-4-methoxyphenol is isolated as a DMAP co-crystal.

In one embodiment, the instant process further comprises a step of reacting the 2-isopropyl-4-methoxyphenol with ClCH$_2$CN to form 2-(2-isopropyl-4-methoxyphenoxy)acetonitrile as shown below:

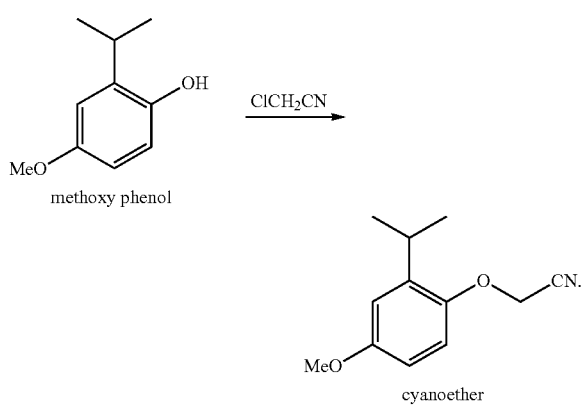

methoxy phenol cyanoether

In one embodiment, the above reaction is carried out in the presence of NMP and toluene. In another embodiment, the reaction is carried out in the presence of acetonitrile. In yet another embodiment, other polar aprotic solvents can be used.

In one embodiment, the above reaction is carried out in the presence of a base. In one embodiment, the base is NaOH. In another embodiment, the base is potassium carbonate. In another embodiment, other hydroxide or carbonate bases can be used.

In one embodiment, chloroacetonitrile is used as an alkylating reagent. In another embodiment, bromoacetonitrile, iodoacetonitrile, and other 2-substituted acetonitriles can be used.

In one embodiment, the above reaction is carried out at a temperature of about 0° C. to about 10° C. In another embodiment, the above reaction is carried out at a temperature of about 25° C. to about 35° C.

In one embodiment, the instant process further comprises a step of converting the cyanoether compound of the following formula to 5-(2-isopropyl-4-methoxyphenoxy)pyrimidine-2,4-diamine:

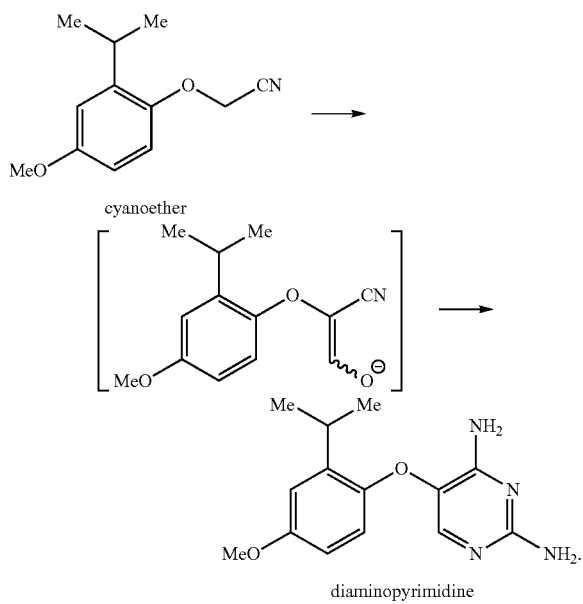

In one embodiment, the above conversion is carried out by first forming a solution of the 2-(2-isopropyl-4-methoxyphenoxy)acetonitrile with ethyl formate in toluene to form a 3-hydroxy-2-(2-isopropyl-4-methoxyphenoxy)acrylonitrile inolate intermediate. In other embodiments, these compounds are dissolved in NMP, DMI, or other polar aprotic solvents.

In one embodiment, the solution containing the enolate intermediate 3-hydroxy-2-(2-isopropyl-4-methoxyphenoxy)acrylonitrile is mixed with a guanidine source directly without isolation of the enolate.

In one embodiment, the source of guanidine is guanidine hydrochloride. In another embodiment, other salt forms of guanidine may be used including guanidine carbonate and guanidine hydrogen sulfate.

In one embodiment, ammonium salts are present during the addition of guanidine.

In one embodiment, toluene is distilled from the reaction mixture prior to crystallization. In other embodiments, toluene is not removed prior to crystallization.

In one embodiment, N-methylpyrrolidinone is used as a solvent. In another embodiment, other polar aprotic solvents are used.

In one embodiment, the above reaction between the mixture and guanidine-HCl is carried out at a temperature of about 80° C. to 98° C. In another embodiment, the reaction temperature is about 95° C. to 110° C.

In one embodiment, 5-(2-isopropyl-4-methoxyphenoxy)pyrimidine-2,4-diamine is isolated as an anhydrate. In another embodiment, 5-(2-isopropyl-4-methoxyphenoxy)pyrimidine-2,4-diamine is isolated as an NMP solvate. 5-(2-isopropyl-4-methoxyphenoxy)pyrimidine-2,4-diamine also forms solvates with acetone, DMA or DMI.

In one embodiment, the instant process further comprises a step of reacting 5-(2-isopropyl-4-methoxyphenoxy)pyrimidine-2,4-diamine with $ClSO_3H$ followed by ammonia to form Compound A free base:

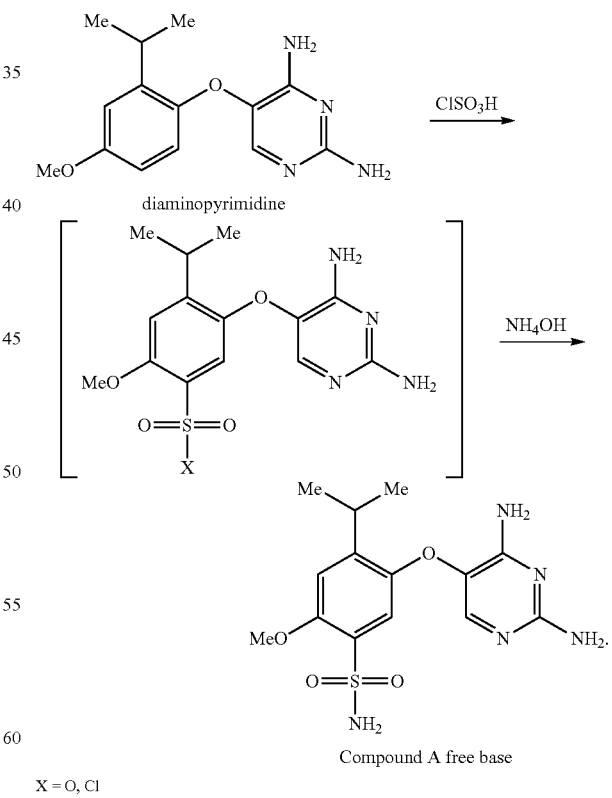

In one embodiment, ammonia is introduced as ammonium hydroxide. In another embodiment, other ammonium salts can be used. In another embodiment, ammonia in organic solvents is used.

In one embodiment, the above reaction between 5-(2-isopropyl-4-methoxyphenoxy)pyrimidine-2,4-diamine and ClSO₃H is carried out in the presence of MeCN.

In one embodiment, the above reaction between 5-(2-isopropyl-4-methoxyphenoxy)pyrimidine-2,4-diamine and ClSO₃H is carried out at a temperature of about 25° C. to about 35° C. In another embodiment, the reaction temperature is about 35° C. to about 45° C. In yet another embodiment, the reaction temperature is about 45° C. to about 70° C.

In one embodiment, methanol is present during the conversion of the sulfonyl chloride to Compound A. In another embodiment, water is present during the conversion of the sulfonyl chloride to Compound A.

In one embodiment, Compound A free base is obtained as an anhydrate. In another embodiment, Compound A free base is obtained as an acetonitrile solvate. Compound A free base also forms solvates with DMSO, DMAc, DMF, acetone, NMP, IPA, methanol, THF, MEK, Sulfolane, or NMP/IPA.

In one embodiment, Compound A free base is obtained at a yield of greater than 80% from the above reactions. In another embodiment, the yield is greater than 85%. In yet another embodiment, the yield is greater than 90%.

In one embodiment, the instant process further comprises a step of converting Compound A free base to a citrate salt of Compound A.

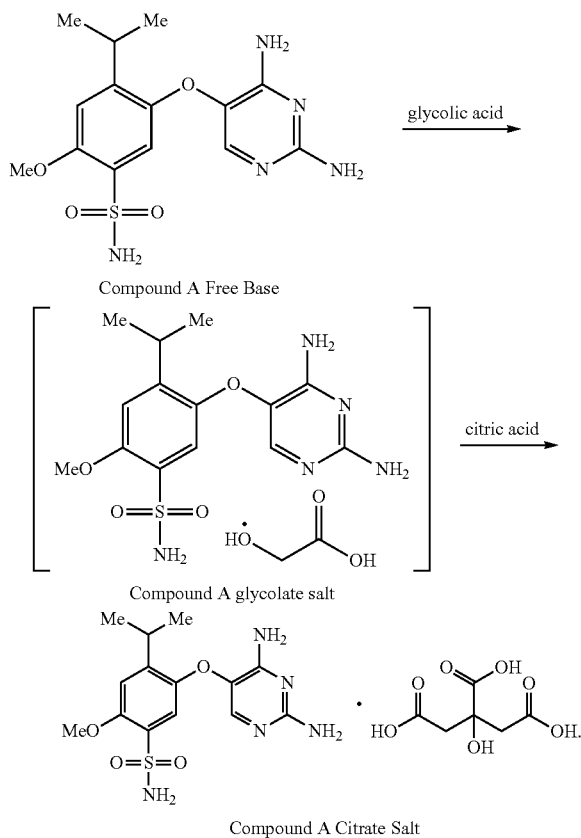

In one embodiment, the conversion is carried out in the presence of MeOH and glycolic acid. In another embodiment, IPA is also present during the conversion.

In one embodiment, the citrate salt is isolated as an anhydrate. In another embodiment, the citrate salt is isolated as a solvate of methanol or isopropanol. The citrate salt also forms solvates with methanol/water, ethanol/water, IPA/water, THF or NMP.

In one embodiment, the glycolate salt is isolated as an anhydrate and then converted to the citrate salt. The glycolate salt also forms solvates or hydrates with methanol, IPA, tert-Amyl alcohol, water or a combination of these solvents, and forms desolvated/dehydrated forms from these solvates/hydrates.

In one embodiment, the above conversion has a yield of greater than 85%. In another embodiment, the yield is greater than 90%. In yet another embodiment, the yield is about 93%.

In one embodiment, a process for preparing a citrate salt of Compound A comprises the following steps:

(a) converting 2-isopropylphenol to a 4-bromo-2-isopropylphenol DABCO co-crystal:

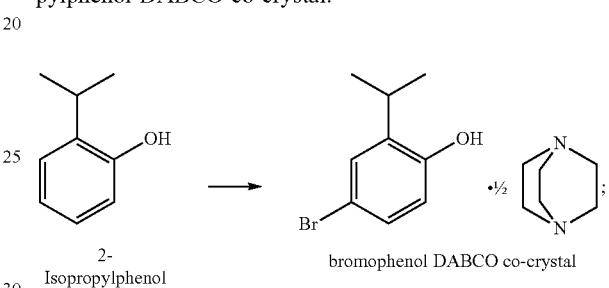

(b) reacting the resulting 4-bromo-2-isopropylphenol DABCO co-crystal with NaOMe to form 2-isopropyl-5-methoxyphenol:

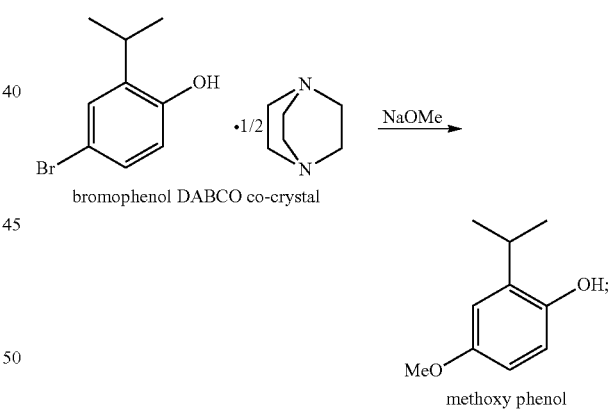

(c) reacting the 2-isopropyl-5-methoxyphenol with ClCH₂CN to form 2-(2-isopropyl-4-methoxyphenoxy)acetonitrile:

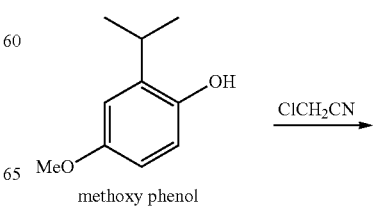

-continued

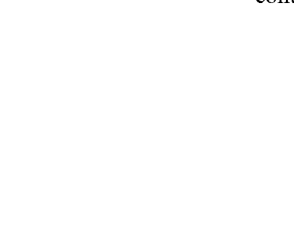
cyanoether (d) converting the 2-(2-isopropyl-4-methoxyphenoxy)acetonitrile to 5-(2-isopropyl-4-methoxyphenoxy)pyrimidine-2,4-diamine:

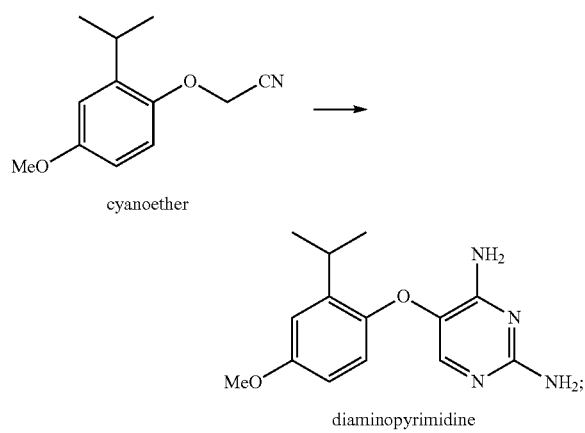
cyanoether diaminopyrimidine (e) reacting the 5-(2-isopropyl-4-methoxyphenoxy)pyrimidine-2,4-diamine with ClSO₃H followed by NH₄OH to form Compound A free base, 5-((2,4-diaminopyrimidin-5-yl)oxy)-4-isopropyl-2-methoxybenzenesulfonamide:

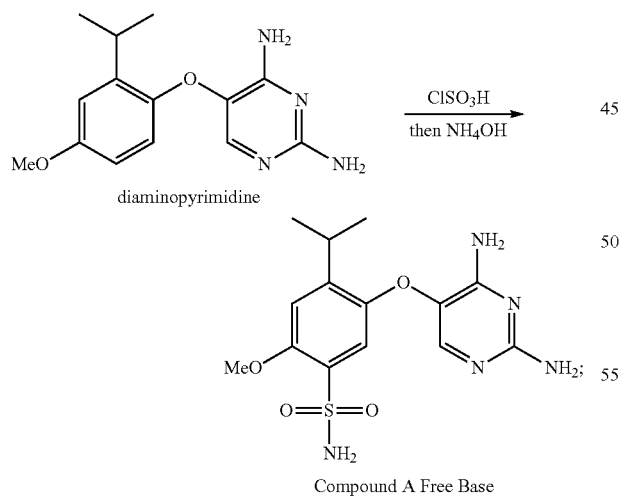
diaminopyrimidine

Compound A Free Base and (f) converting Compound A free base, 5-((2,4-diaminopyrimidin-5-yl)oxy)-4-isopropyl-2-methoxybenzenesulfonamide, to Compound A citrate salt in the presence of glycolic acid and MeOH:

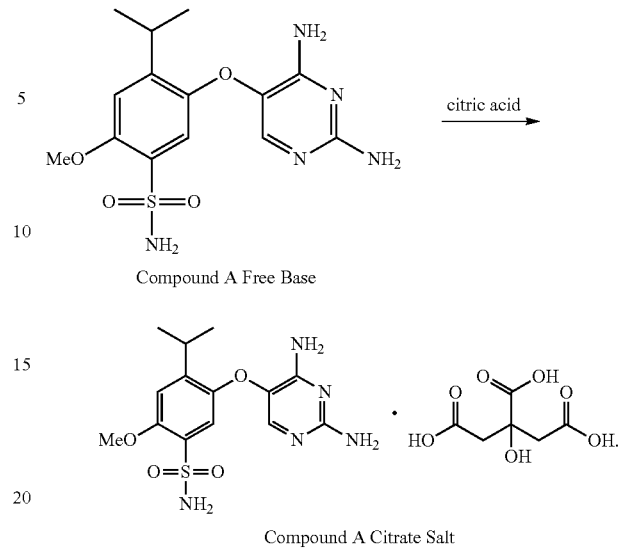
Compound A Free Base

Compound A Citrate Salt

In one embodiment, the overall yield from 2-isopropylphenol to the citrate salt of Compound A is greater than 50%. In another embodiment, the overall yield is greater than 55%. In yet another embodiment, the overall yield is greater than 60%.

EXPERIMENTAL

The following examples are intended to be illustrative only and not limiting in any way. Abbreviations used herein and in the specification are those conventional in the art or the following.

° C. degree Celsius
DABCO 1,4-diazabicyclo[2.2.2]octane
DMA dimethylamine
DMAP dimethylaminopyridine
DMF N,N-dimethylformamide
DMI 1,3-dimethyl-2-imidazolidinone
EtOAc ethyl acetate
EtOH ethanol
g gram
h hour(s)
IPA isopropyl alcohol
kg kilogram
L liter
LC liquid chromatography
MeOH methanol
MSA methane sulfonic acid
MeCN acetonitrile
MEK methyl ethyl ketone
min minutes
mL or ml milliliter(s)
mol moles
N normal
NBS N-bromo succinimide
nM nanomolar
NMP N-methyl-2-pyrrolidone
RT or rt room temperature
sat. saturated
THF tetrahydrofuran wt or wt. weight
XRPD X-ray powder diffraction In one embodiment, Compound A free base and its citrate salt are obtained by a process comprising synthesis and isolation of a 4-bromo-2-isopropylphenol DABCO co-crystal, synthesis of 2-isopropylphenyl, 2-isopropyl-5-methoxyphenol and 2-(2-isopropyl-4-methoxyphenoxy)acetonitrile, synthesis and isolation of the 5-(2-isopropyl-4-methoxyphenoxy)pyrimidine-2,4-diamine, synthesis of Compound A free base, and final conversion of Compound A free base to the corresponding citrate salt, as illustrated below.

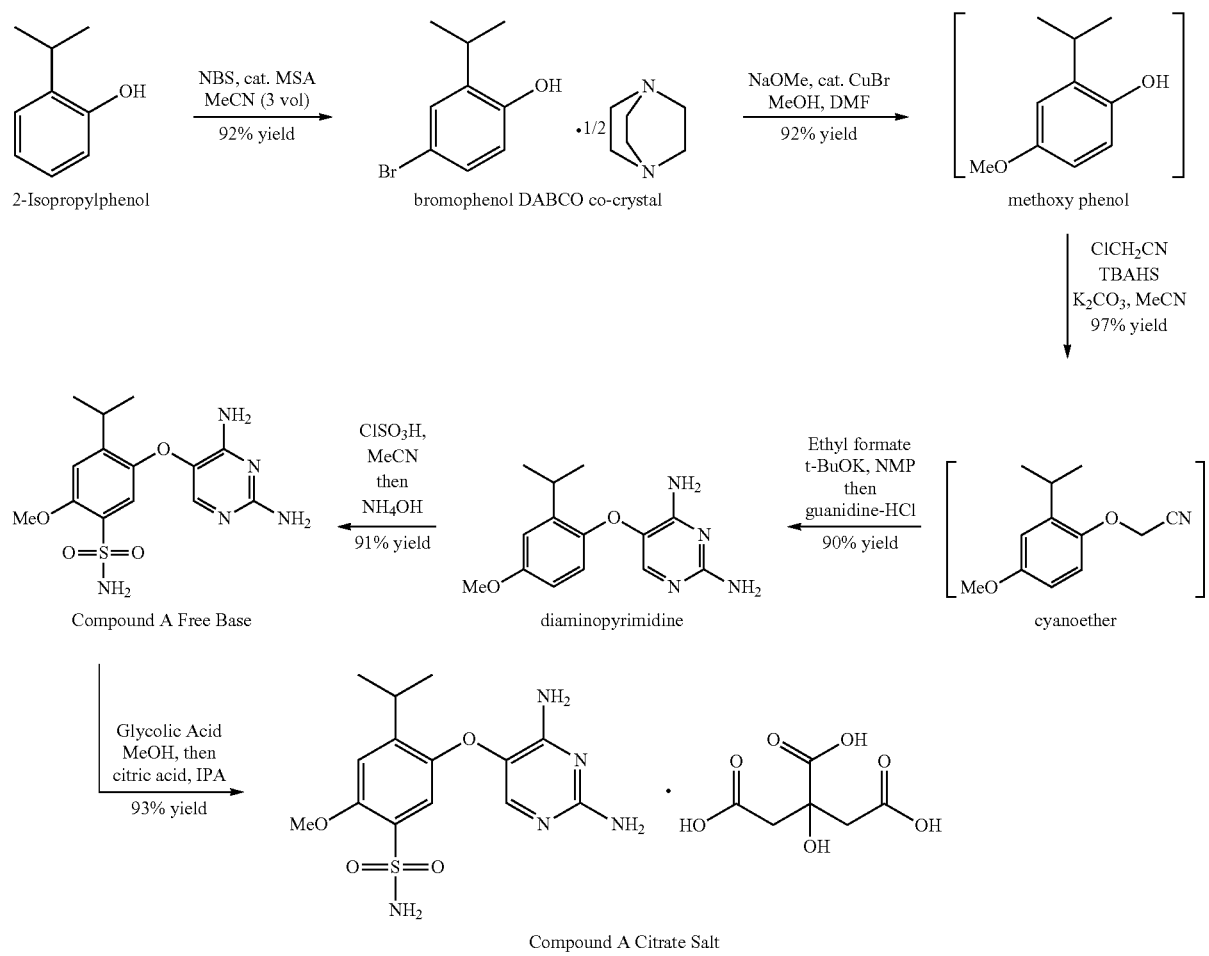

To a solution of 2-isopropyl phenol (75.0 g, 550 mmol) in acetonitrile (225 mL) was added MSA (0.520 g, 5.41 mmol).

Step 1. Preparation of 4-Bromo-2-isopropylphenol DABCO Co-Crystal

The following 4-bromo-2-isopropylphenol hemi-DABCO co-crystal is obtained in greater than 99% purity and at about 85-92% yield by the following process:

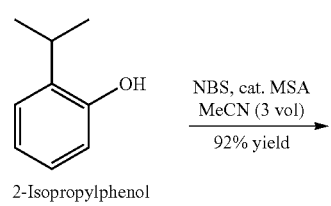

The mixture was cooled to −10° C. and NBS (98.01 g, 550 mmol) was added in portions while maintaining the internal temperature below 10° C. The reaction was aged for 30 min to 1 h and then warmed to 20° C., diluted with water (450 mL), and extracted with toluene (225 mL). The organic layer was sequentially washed with 9 wt % phosphoric acid (150 mL) and 5 wt % NaCl (150 mL). The organic layers were concentrated to roughly 150 mL and filtered into a clean reactor. The mixture was heated to 30-40° C. and n-heptane (28.5 mL) was added followed by DABCO (30.89 g, 275 mmol). The mixture was seeded (a seed can be synthesized from a previous batch of this procedure preformed without seeding) with 4-bromo-2-isopropylphenol hemi-DABCO co-crystal (75 mg, 0.277 mmol), diluted with 52.5 mL of n-heptane, and stirred for 1 h. The slurry was cooled to 20°

C. over 1 h and 370 mL of n-heptane is added over 2 h. The slurry was cooled to 5° C. over 2 h, aged for 2 h, filtered, and washed with n-heptane (2×75 mL). The solid was dried at 20-25° C. under vacuum to yield 4-bromo-2-isopropylphenol hemi-DABCO co-crystal (134.8 g, 90%) as a solid. ¹H NMR (400 MHz, DMSO-d₆) δ 7.20 (d, J=2.5 Hz, 1H), 7.13 (dd, J=8.5, 2.6 Hz, 2H), 6.73 (d, J=8.5 Hz, 2H), 3.16 (hept, J=6.9 Hz, 2H), 2.60 (s, 12H), 1.14 (d, J=6.9 Hz, 12H).

The crystallization of step 1 generates 4-bromo-2-isopropylphenol hemi-DABCO co-crystal, bromophenol mono-DABCO co-crystal, or a mixture of bromophenol hemi-DABCO co-crystal and bromophenol mono-DABCO co-crystal. An XRPD pattern of bromophenol hemi-DABCO co-crystal is shown in FIG. 1.

The bromo-phenol mono-DABCO co-crystal can be generated in the following procedure:

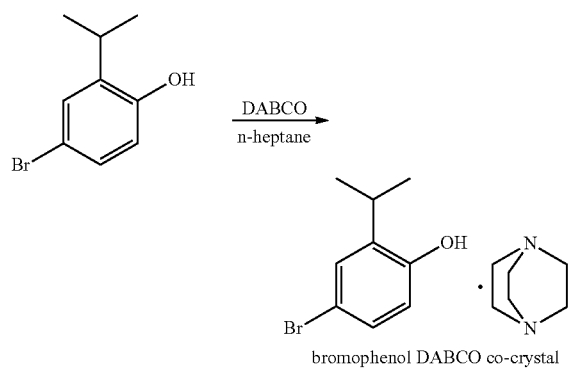

To a vial with a stir bar was charged DABCO (1.7 g, 15 mmol), phenol (2.5 g, 15 mmol), and 2 mL of n-heptane. The resulting slurry was stirred at 23° C. overnight. The slurry was then filtered and the resulting wet cake was washed with 2 mL of 5° C. n-heptane. The cake was dried under vacuum with nitrogen sweep to afford 4-bromo-2-isopropylphenol mono-DABCO co-crystal (2.9 g, 70% yield) as a solid. ¹H NMR (500 MHz, DMSO-d₆) δ 9.65 (s, 1H), 7.20 (s, 1H), 7.14 (d, J=8.5 Hz, 1H), 6.74 (d, J=8.5 Hz, 1H), 3.17 (hept, J=6.8 Hz, 1H), 2.61 (s, 12H), 1.15 (d, J=6.9 Hz, 6H).

Figure 2:
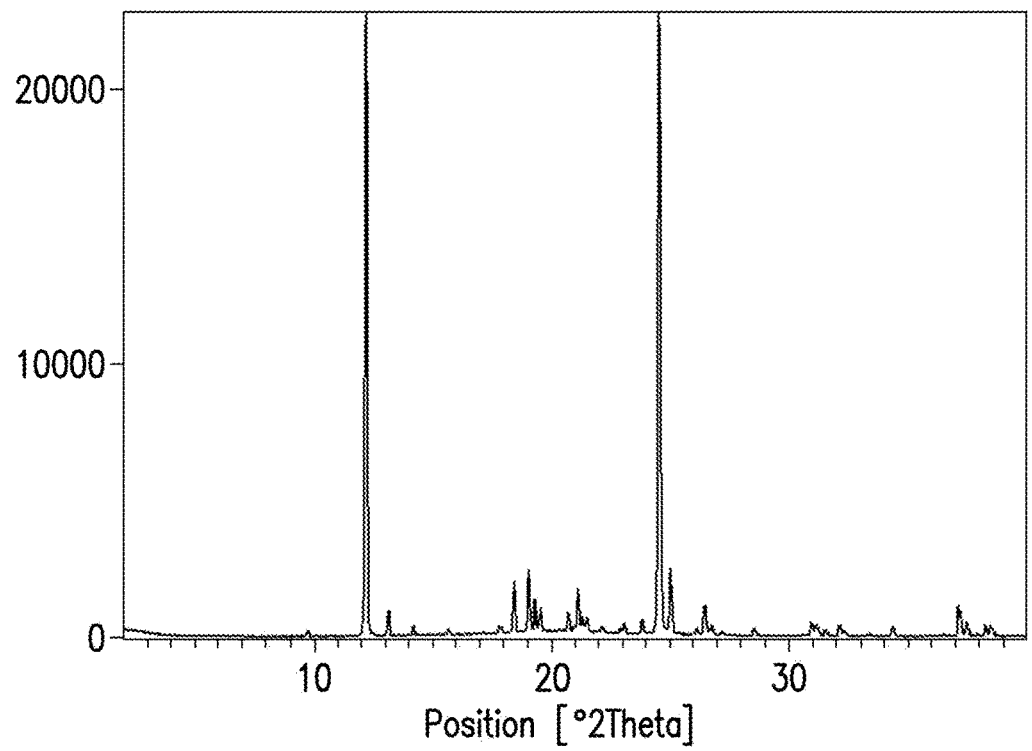
FIG. 2. An XRPD pattern of 4-bromo-2-isopropylphenol mono-DABCO co-crystal.

An XRPD pattern of bromophenol mono-DABCO co-crystal is shown in FIG. 2.

Step 2a. Preparation of 2-Isopropyl-4-Methoxyphenol

The 2-isopropyl-4-Methoxyphenol shown below is obtained at about 92% yield by the following process:

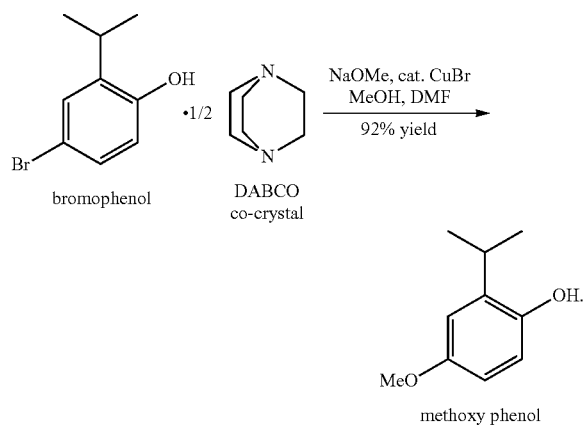

To a solution of 4-bromo-2-isopropylphenol hemi-DABCO co-crystal (120 g, 442 mmol) in 25 wt % sodium methoxide in methanol (430 g) was added 60 mL of DMF. The solution was pressure purged with nitrogen, copper (I) bromide (3.23 g, 22.5 mmol) was added to the mixture, and the reaction was heated to reflux for 12-16 h. The reaction is cooled to 0-5° C. and quenched with 6M HCl until the pH of the solution is less than 5. The slurry is diluted with 492 mL of toluene and 720 mL of water to provide a homogeneous solution with a rag between the layers. The aqueous layer is cut to waste. The organic layer is filtered to remove the rag and washed with 240 mL of water to provide 2-isopropyl-4-methoxylphenol (491 g, 13.3 wt %, 89% assay yield) as a solution in toluene. ¹H NMR (500 MHz, DMSO-d₆) δ 8.73 (s, 1H), 6.68 (d, J=8.6 Hz, 1H), 6.66 (d, J=3.0 Hz, 1H), 6.55 (dd, J=8.6, 3.1 Hz, 1H), 3.65 (s, 3H), 3.17 (hept, J=6.9 Hz, 1H), 1.14 (d, J=6.9 Hz, 6H).

Step 2b. Preparation of 2-Isopropyl-4-Methoxyphenol

Alternatively, the methoxy phenol is obtained by the following process:

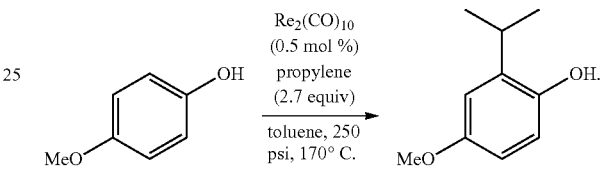

To a high-pressure vessel were charged 400 mL of anhydrous toluene, Re₂(CO)₁₀ (3.16 g, 4.84 mmol) and mequinol (100 g, 806 mmol) at RT. The vessel was then degassed with propylene, and charged with propylene (85.0 g, 2.02 mol). The vessel was sealed and heated to 170° C. Internal pressure was measured near 250 psi. The reaction was stirred at this condition for 72 h. The vessel was then allowed to cool down to 23° C. The internal pressure was carefully released to 1 atmospheric pressure, and the toluene solution was assayed as 91% and used directly in the next step or isolated as a solid.

Figure 3:
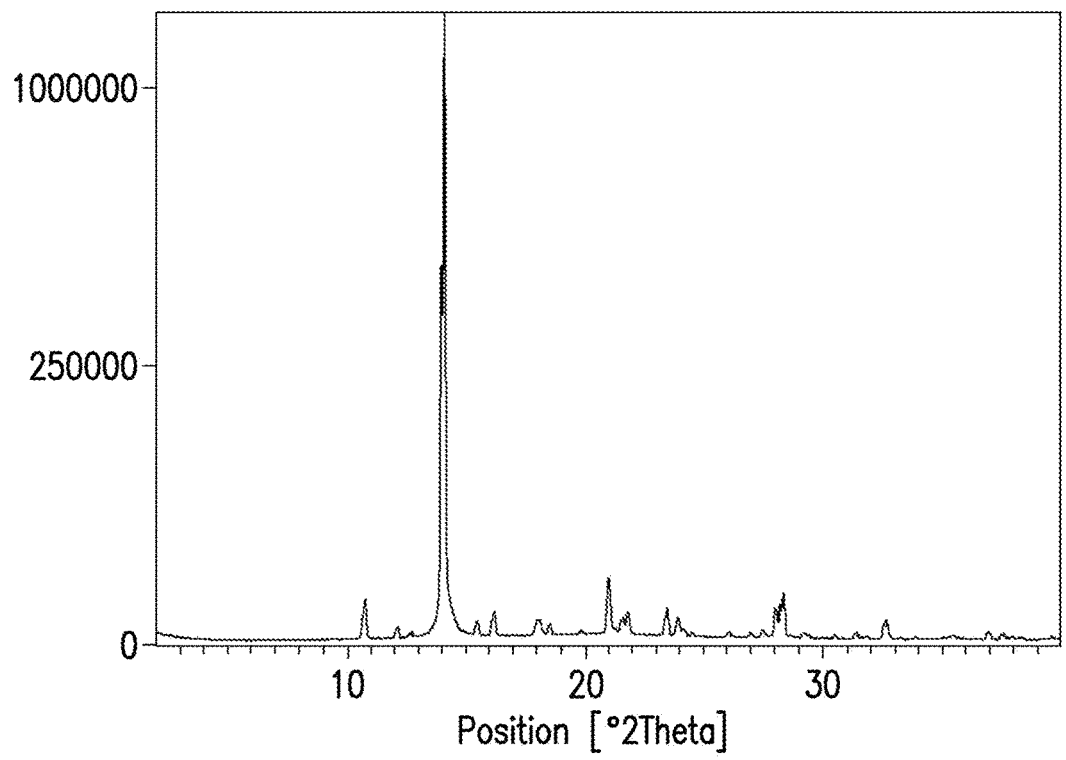
FIG. 3. An XRPD pattern of 2-isopropyl-4-methoxyphenol form 1.

Step 2a/2b results in anhydrous 2-isopropyl-4-methoxyphenol form 1. An XRPD pattern of the methoxy phenol form 1 is shown in FIG. 3.

In another embodiment, the product is isolated as a DMAP co-crystal:

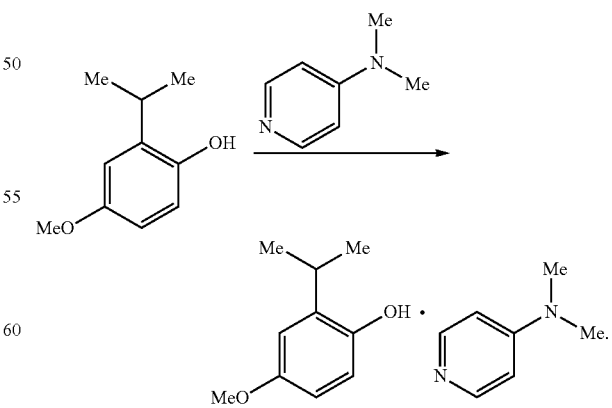

To a vial with a stir bar was charged DMAP (3.67 g, 30.1 mmol), 2.5 ml of toluene, and 2-isopropyl-4-methoxylphenol (5.00 g, 30.1 mmol). The reaction mixture was stirred at RT for 5 min, and a homogeneous solution was formed. The reaction mixture was then cooled to 5° C. Ten mL of n-heptane was slowly charged over 20 min. The resulting slurry was stirred at 5° C. overnight. The slurry was filtered and the resulting wet cake was washed with 3 mL of 5° C. n-heptane. The cake was dried under vacuum with a nitrogen sweep to provide 2-isopropyl-4-methoxylphenol DMAP co-crystal (7.01 g, 81%) as a solid. $^1$H NMR (500 MHz, DMSO-$d_6$) δ 8.78 (s, 1H), 8.10 (d, J=6.1 Hz, 2H), 6.71-6.65 (m, 2H), 6.57 (dd, J=11.3, 6.0 Hz, 3H), 3.66 (s, 3H), 3.17 (hept, J=6.8 Hz, 1H), 2.95 (s, 6H), 1.14 (d, J=6.9 Hz, 6H).

Figure 4:
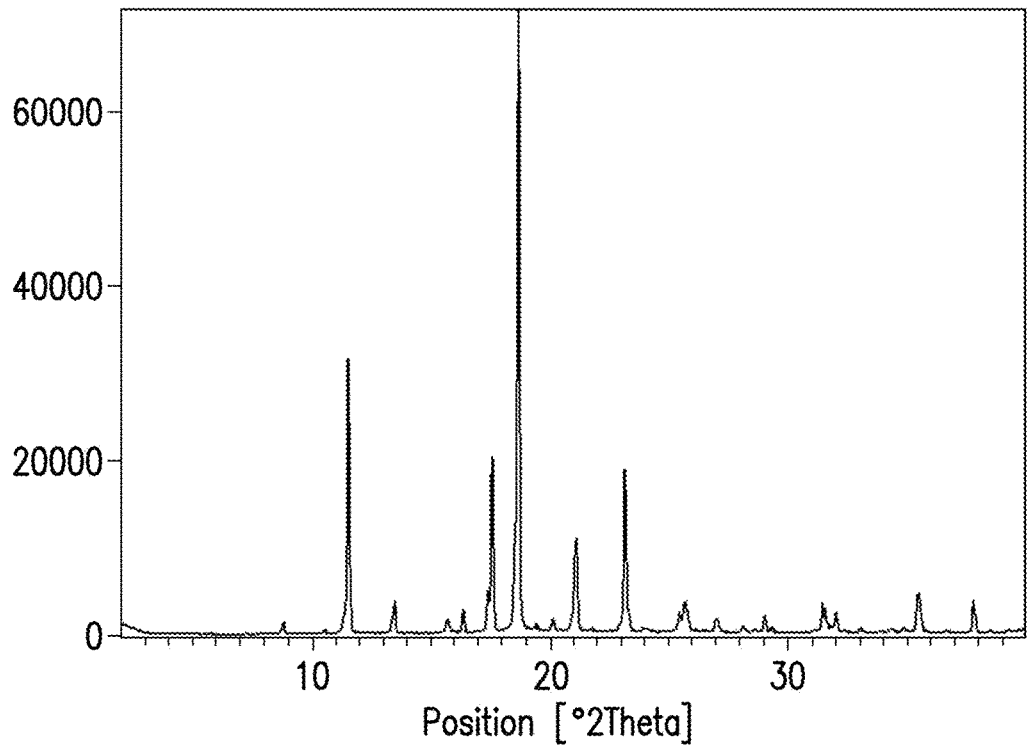
FIG. 4. An XRPD pattern of 2-isopropyl-4-methoxyphenol DMAP co-crystal.

The crystallization generates anhydrous 2-isopropyl-4-methoxyphenol DMAP co-crystal. An XRPD pattern of the 2-isopropyl-4-methoxyphenol DMAP co-crystal is shown in FIG. 4.

Step 3a. Preparation of the Cyanoether, 2-(2-isopropyl-4-methoxyphenoxy)acetonitrile The cyanoether is obtained at about 95% yield by the following process:

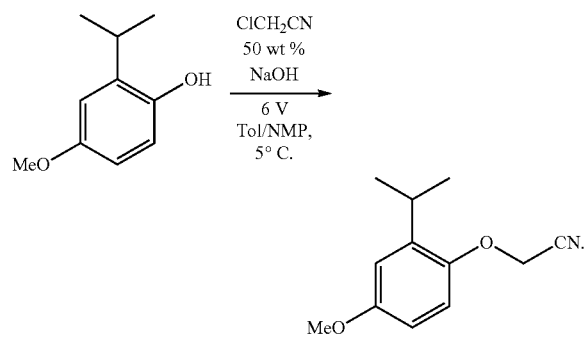

A 12-15 wt % solution of 2-isopropyl-4-methoxylphenol (314.3 g, 12 wt %, 226.8 mmol) was concentrated to greater than 50 wt % 2-isopropyl-4-methoxyphenol in toluene under vacuum at 40-50° C. To the solution was added 189 mL of NMP, and the mixture was cooled to 5° C. Sodium hydroxide (27.2 g, 50 wt % in water, 340 mmol) and chloroacetonitrile (36 g, 340 mmol) were added sequentially to the mixture while maintaining the internal temperature below 10° C. The reaction was aged for 2 h and then diluted with 150 mL of toluene and 226 mL of water while maintaining the temperature below 10° C. The mixture was warmed to 20-25° C., the layers were separated, and the organic layer was washed with 75 mL of 20 wt % NaCl (aq.). The organic layer was and filtered to provide 2-(2-isopropyl-4-methoxyphenoxy)acetonitrile (56.8 g, 74.6 wt %) as a solution in toluene. The filter was washed with NMP to provide additional 2-(2-isopropyl-4-methoxyphenoxy)acetonitrile (27.1 g, 5.0 wt %) as a solution in NMP. The combined yield was about 94%. $^1$H NMR (500 MHz, DMSO-$d_6$) δ 7.05 (d, J=8.8 Hz, 1H), 6.81 (d, J=3.0 Hz, 1H), 6.78 (dd, J=8.8, 3.1 Hz, 1H), 5.11 (s, 2H), 3.73 (s, 3H), 3.20 (hept, J=6.9 Hz, 1H), 1.17 (d, J=6.9 Hz, 6H).

Step 3b. Preparation of the Cyanoether, 2-(2-isopropyl-4-methoxyphenoxy)acetonitrile Alternatively, the cyanoether shown below is obtained at about 92% yield by the following process:

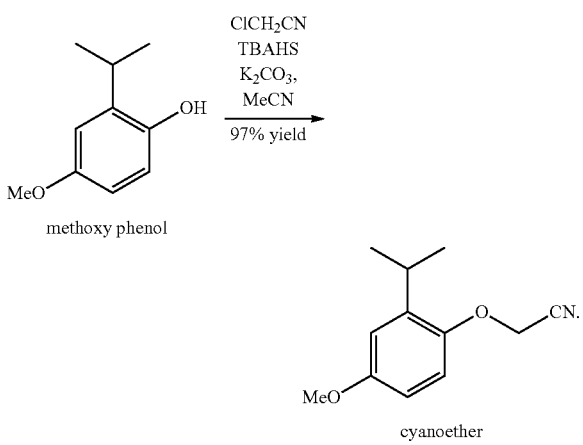

A solution of 2-isopropyl-4-methoxyphenol in toluene (491 g, 13.3 wt %, 393 mmol) was concentrated and solvent switched to acetonitrile under vacuum at 40-50° C. Potassium carbonate (164.5 g, 1190 mmol) and tetrabutylammonium hydrogensulfate (1.5 g, 4.42 mmol) were added to a separate vessel, and the vessel was pressure purged with nitrogen gas. The solution of phenol in acetonitrile and chloroacetonitrile was added sequentially to the reaction vessel. The vessel was heated to 40° C. and aged for 4 h. The mixture was allowed to cool to 25° C., and was diluted with 326 mL water. The layers were separated, and the organic layer was washed with 130 mL of 10 wt % NaCl. A solvent switch to toluene was performed under vacuum, and the organic layer was filtered through two 16D Cuno #5 cartridges. The organic layer was concentrated to provide 2-(2-isopropyl-4-methoxyphenoxy)acetonitrile in toluene (128.2 g, 58 wt %, 92% yield).

Step 4. Preparation of the Diaminopyrimidine, 5-(2-isopropyl-4-methoxyphenoxy)pyrimidine-2,4-diamine The diaminopyrimidine is obtained at about 90% yield by the following process:

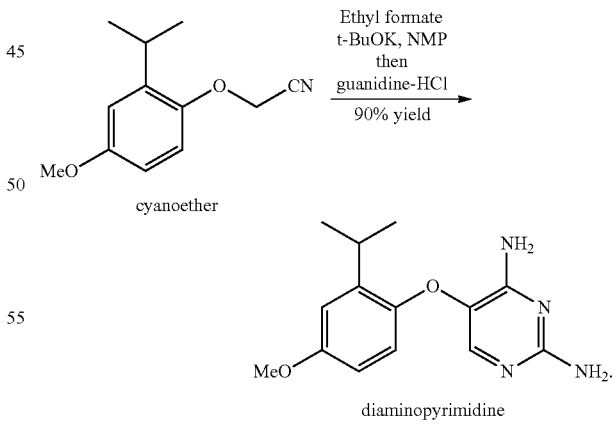

A solution of potassium tert-butoxide (44.8 g, 0399 mmol) in NMP (180 mL) was cooled to −10° C. A solution of 2-(2-isopropyl-4-methoxyphenoxy)acetonitrile, the cyanoether, (59.3 g, 61.4 wt %, 177 mmol) in toluene and ethyl formate (26.3 g, 355 mmol) was charged to the base solution while maintaining the internal temperature between −12° C. and −8° C. After a 3 h age, guanidine hydrochloride (136 g, 1420 mmol) was added to the mixture and the reaction was heated to 115° C. for 6 h. The mixture was allowed to cool to 90° C., diluted with 200 mL of water, and aged until the reaction mixture was homogeneous (about 30-45 min). After all solids dissolved, vacuum (400 mm Hg) was applied to the reactor to remove toluene. Vacuum was disconnected and the solution was allowed to cool to 85° C. 5-(2-Isopropyl-4-methoxyphenoxy)pyrimidine-2,4-diamine seed (49.8 mg) (a seed can be synthesized by a route described in U.S. Pat. No. 7,741,484) was charged, the solution was aged for 2 h, 200 mL of water was added, and the batch was allowed to cool to 20° C. over 6 h. The slurry was aged for 10 h at 20° C., filtered, washed with 2:1 water:NMP (3×100 mL) and water (3×100 mL), and dried under vacuum at 50° C. to provide the title compound (42.2 g, 88%) as a solid. $^1$H NMR (500 MHz, DMSO-$d_6$) δ 7.23 (s, 1H), 6.83 (d, J=3.0 Hz, 1H), 6.70 (dd, J=8.9, 3.0 Hz, 1H), 6.63 (d, J=8.8 Hz, 1H), 6.32 (s, 2H), 5.75 (s, 2H), 3.71 (s, 3H), 3.28 (hept, J=6.9 Hz, 1H), 1.20 (d, J=6.9 Hz, 6H); $^{13}$C NMR (126 MHz, DMSO-$d_6$) δ 159.7, 157.2, 155.1, 148.4, 144.2, 139.0, 130.4, 116.9, 112.5, 111.3, 55.4, 26.57, 22.83.

Figure 5:
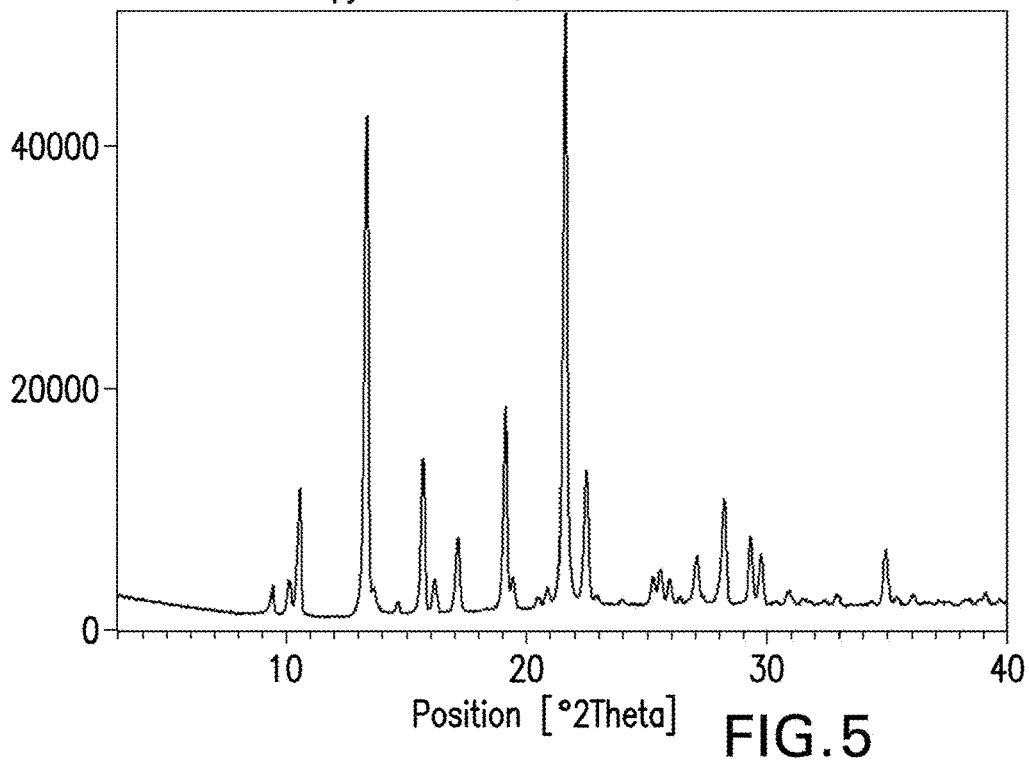
FIG. 5. An XRPD pattern of 5-(2-isopropyl-4-methoxyphenoxy)pyrimidine-2,4-diamine form 1.

The crystallization of step 4 generates an anhydrous 5-(2-isopropyl-4-methoxyphenoxy)pyrimidine-2,4-diamine form 1. An XRPD pattern of the 5-(2-isopropyl-4-methoxyphenoxy)pyrimidine-2,4-diamine form 1 is shown in FIG. 5.

Figure 6:
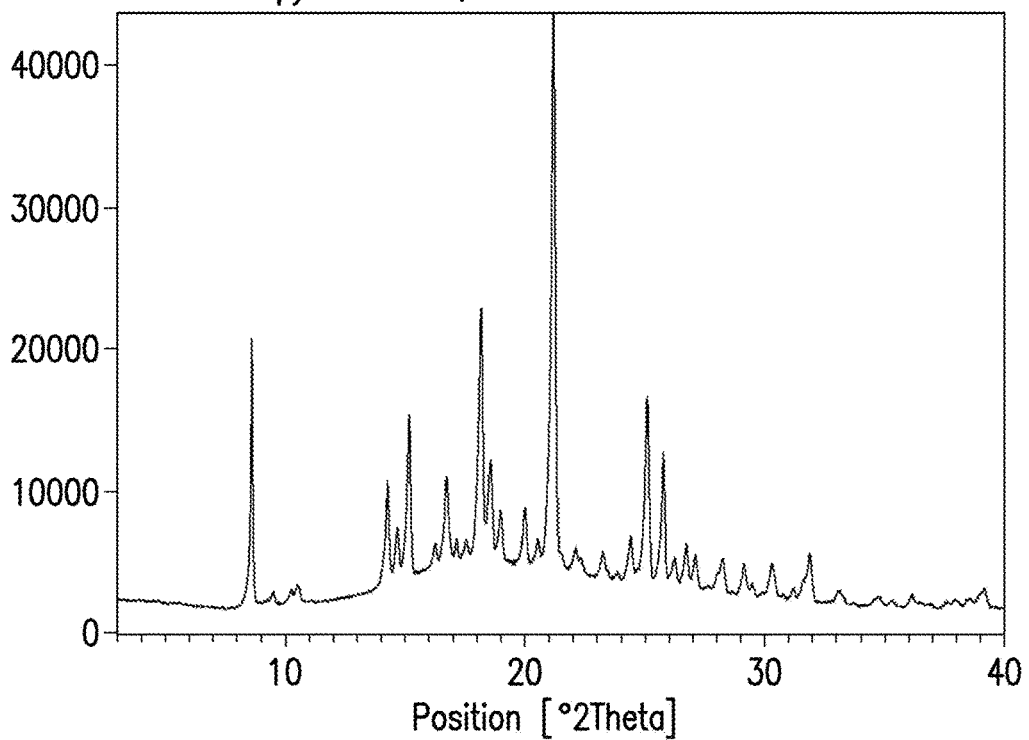
FIG. 6. An XRPD pattern of 5-(2-isopropyl-4-methoxyphenoxy)pyrimidine-2,4-diamine NMP solvate 1.

In one embodiment, 5-(2-isopropyl-4-methoxyphenoxy) pyrimidine-2,4-diamine NMP solvate 1 is obtained by adding excess amount of 5-(2-isopropyl-4-methoxyphenoxy) pyrimidine-2,4-diamine form 1 into NMP in a closed vessel to form a suspension. The suspension is stirred at RT until the completion of form transition. The crystals of 5-(2-isopropyl-4-methoxyphenoxy)pyrimidine-2,4-diamine NMP solvate 1 can be collected by filtration and measured immediately by XRPD to prevent desolvation. An XRPD pattern of the 5-(2-isopropyl-4-methoxyphenoxy)pyrimidine-2,4-diamine NMP solvate 1 is shown in FIG. 6.

Step 5. Preparation of Compound A Free Base

Compound A free base is obtained at about 91% yield by a process comprising the steps:

for 1 h at 25° C. and then heated to 45° C. for 12 h. The solution was allowed to cool to 20° C. and added to a solution of 235 mL ammonium hydroxide and 71 mL of acetonitrile at −10° C. while maintaining the internal temperature below 15° C. The slurry was aged at 10° C. for 1 h, heated to 25° C., and aged for 1 h. The slurry was diluted with 564 mL of water and 188 mL of 50 wt % sodium hydroxide to provide a homogeneous solution that was heated to 35° C. for 2 h. The solution was allowed to cool to 22° C. and the pH of the solution was adjusted to 12.9 with a 2M solution of citric acid. The solution was seeded with Compound A free base (470 mg, 1.19 mmol) (a seed can be synthesized by a route described in U.S. Pat. No. 7,741,484), aged for 2 h, acidified to pH 10.5-11.3 with a 2M solution of citric acid over 5-10 h, and then aged for 2 h. The slurry was filtered, the resulting cake was washed with 90:10 water:acetonitrile (2×118 mL) and water (2×235 mL), and dried at 55° C. under vacuum to provide Compound A free base (50.9 g, 91%) as a solid. $^1$H NMR (500 MHz, DMSO-$d_6$) δ 7.36 (s, 1H), 7.07 (s, 1H), 7.05-6.89 (m, 3H), 6.37 (s, 2H), 5.85 (s, 2H), 3.89 (s, 3H), 3.41 (hept, J=6.6 Hz, 1H), 1.27 (d, J=6.8 Hz, 6H).

The crystallization of step 5 generates anhydrous Compound A free base form 1.

Figure 7:
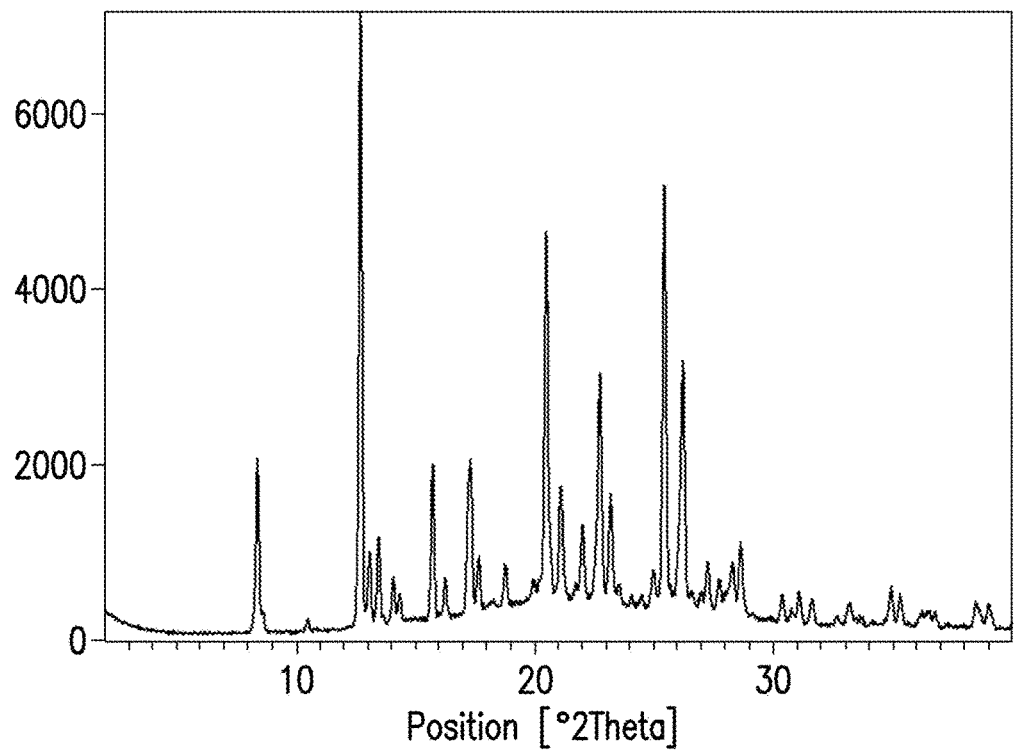
FIG. 7. An XRPD pattern of Compound A free base acetonitrile solvate 1.

In one embodiment, Compound A free base acetonitrile solvate 1 can be prepared by adding excess amount of Compound A free base form 1 into acetonitrile in a closed vessel to form a suspension. The suspension is stirred at 50° C. until the completion of form transition. The crystals of Compound A free base acetonitrile solvate 1 can be collected by filtration and measured immediately by XRPD to prevent desolvation. An XRPD pattern of Compound A free base acetonitrile solvate 1 is shown in FIG. 7.

Step 6a. Preparation of Compound A Citrate Salt

Compound A citrate salt is obtained by a process comprising the steps:

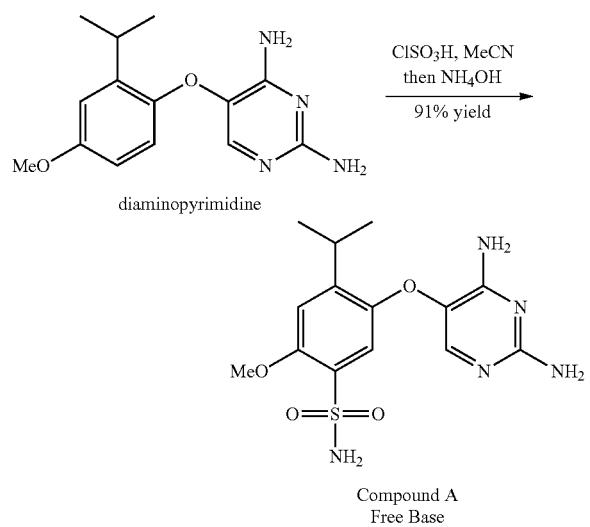

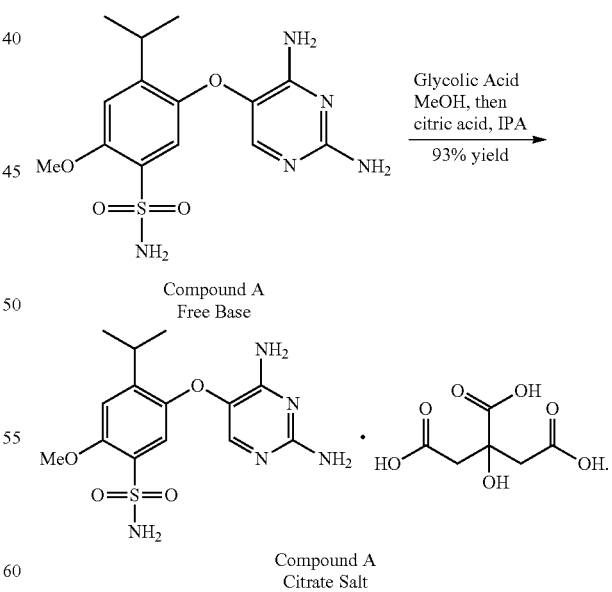

To a suspension of 5-(2-isopropyl-4-methoxyphenoxy) pyrimidine-2,4-diamine, the diaminopyrimidine, (47.0 g, 171 mmol) in 141 mL of acetonitrile at −10° C. was added chlorosulfonic acid (63.1 mL, 942 mmol) while maintaining the internal temperature below 25° C. The solution was aged Compound A free base (30.0 g, 84.9 mmol) and glycolic acid (22.6 g, 297 mmol) were added to methanol (360 mL). The solution was heated to 60° C., aged for 1 h, and filtered through a 0.6 μm filter into a clean vessel. A solution of citric acid (32.6 g, 170 mmol) in 2-propanol (180 mL) at RT was filtered through a 0.6 μm filter into the methanol solution over 30 min while the temperature of the methanol solution was maintained between 58-62° C. The solution was seeded with Compound A citrate salt (450 mg, 0.825 mmol) (a seed can be synthesized by a route described in patent application number PCT/US17/66562), aged for 1 h, and diluted with 180 mL of 2-propanol over 3 h while the temperature was maintained between 58-62° C. The slurry was cooled to 50° C. over 3 h. The slurry was filtered at 50° C., washed with 1:1 methanol:2-propanol (120 mL) and 2-propanol (120 mL) at 50° C., and dried under vacuum at 35° C. to provide Compound A citrate salt (45.1 g, 97%) as a solid. $^1$H NMR (400 MHz, DMSO-$d_6$) δ 10.89 (s, 3H), 7.33 (s, 1H), 7.10 (s, 1H), 7.07 (s, 3H), 7.04 (s, 2H), 6.44 (s, 2H), 3.91 (s, 3H), 3.34 (hept, J=6.7 Hz, 1H), 2.69 (d, J=15.3 Hz, 2H), 2.60 (d, J=15.3 Hz, 2H), 1.26 (d, J=6.9 Hz, 6H).

Step 6b. Alternative preparation of Compound A Citrate Salt

Alternatively, Compound A citrate salt is obtained by a process comprising the steps:

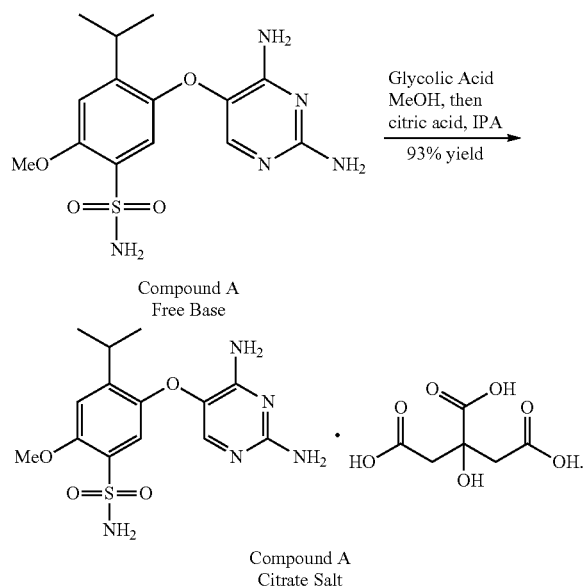

To a suspension of Compound A citrate salt (4.5 g, 8.25 mmol) in methanol (72 mL) and 2-propanol (36 mL) at 50° C. were added simultaneously through separate 0.6 μm filters a solution of Compound A free base (30.0 g, 84.9 mmol) and glycolic acid (22.6 g, 297 mmol) in 360 mL of methanol at 50° C. and a solution of citric acid (19.5 g, 101 mmol) in 180 mL of 2-propanol at 25° C. over 8 h while maintaining the seed solution temperature of 60° C. After the simultaneous addition is complete, citric acid (13.2 g, 68.7 mmol) in 180 mL of 2-propanol was added to the slurry over 8 h while the temperature was maintained at 60° C. The slurry was allowed to cool to 50° C. and aged for 1 h, filtered at 50° C., washed with 1:1 methanol:2-propanol (2×120 mL) and 2-propanol (120 mL), and dried under vacuum at 35° C. to provide Compound A citrate salt (45.1 g, 88%) as a solid.

The crystallization of step 6a/6b generates anhydrous Compound A citrate form 1.

Figure 8:
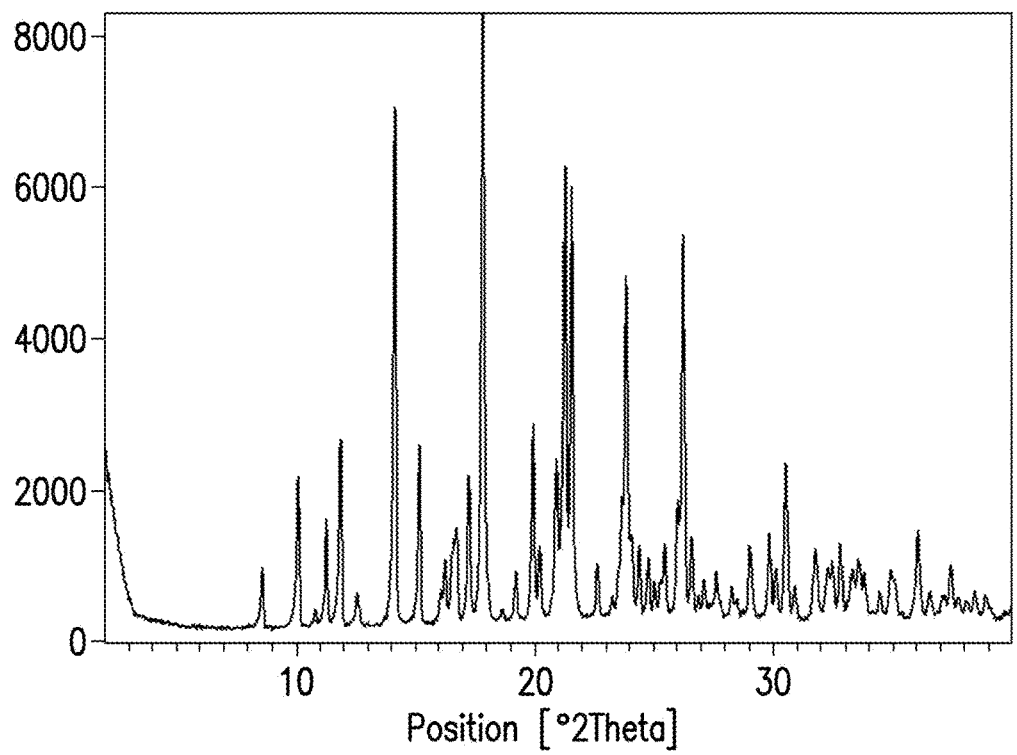
FIG. 8. An XRPD pattern of Compound A citrate methanol solvate 1.

In another embodiment, Compound A citrate methanol solvate 1 can be prepared via a saturated solution of Compound A citrate form 1 in methanol at 50 C. The solution is naturally cooled to ambient temperature or evaporated at ambient temperature until the crystals of Compound A citrate methanol solvate 1 can be acquired. An XRPD pattern of Compound A citrate methanol solvate 1 is shown in FIG. 8.

Figure 9:
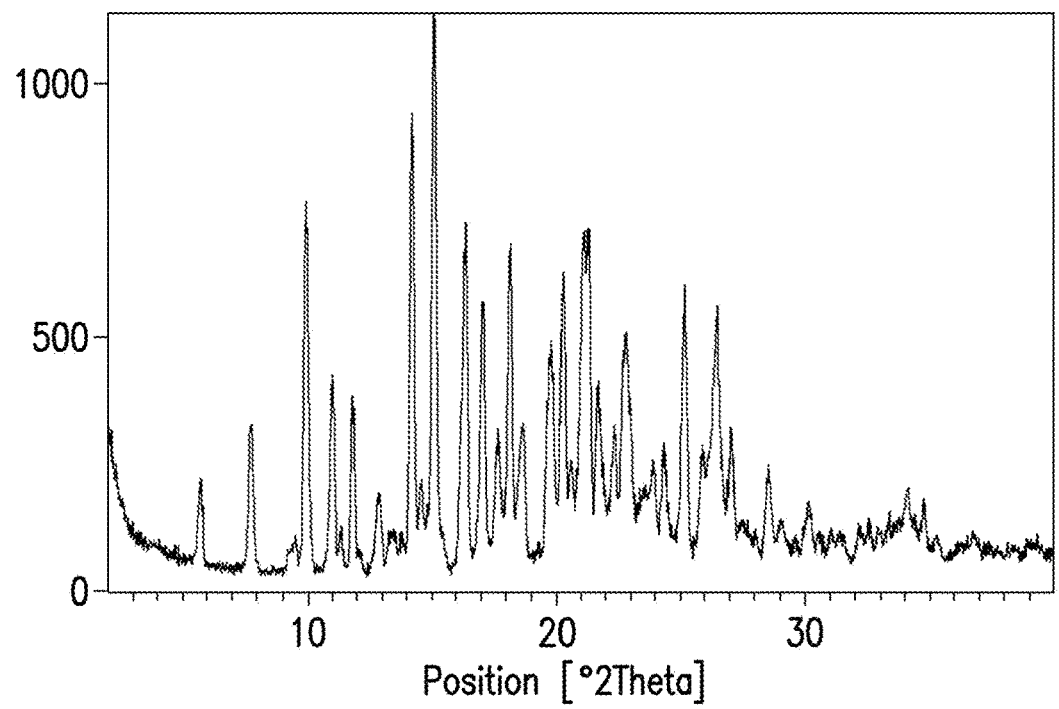
FIG. 9. An XRPD pattern of Compound A citrate IPA solvate 1.

In another embodiment, Compound A citrate IPA solvate 1 can be prepared by adding an excess amount of Compound A citrate methanol solvate 1 into IPA in a closed vessel to form a suspension. The suspension is stirred at 5° C. or lower until the completion of form transition. The crystals of Compound A citrate IPA solvate 1 can be collected by filtration and measured immediately by XRPD to prevent desolvation. An XRPD pattern of Compound A citrate IPA solvate 1 is shown in FIG. 9.

Figure 10:
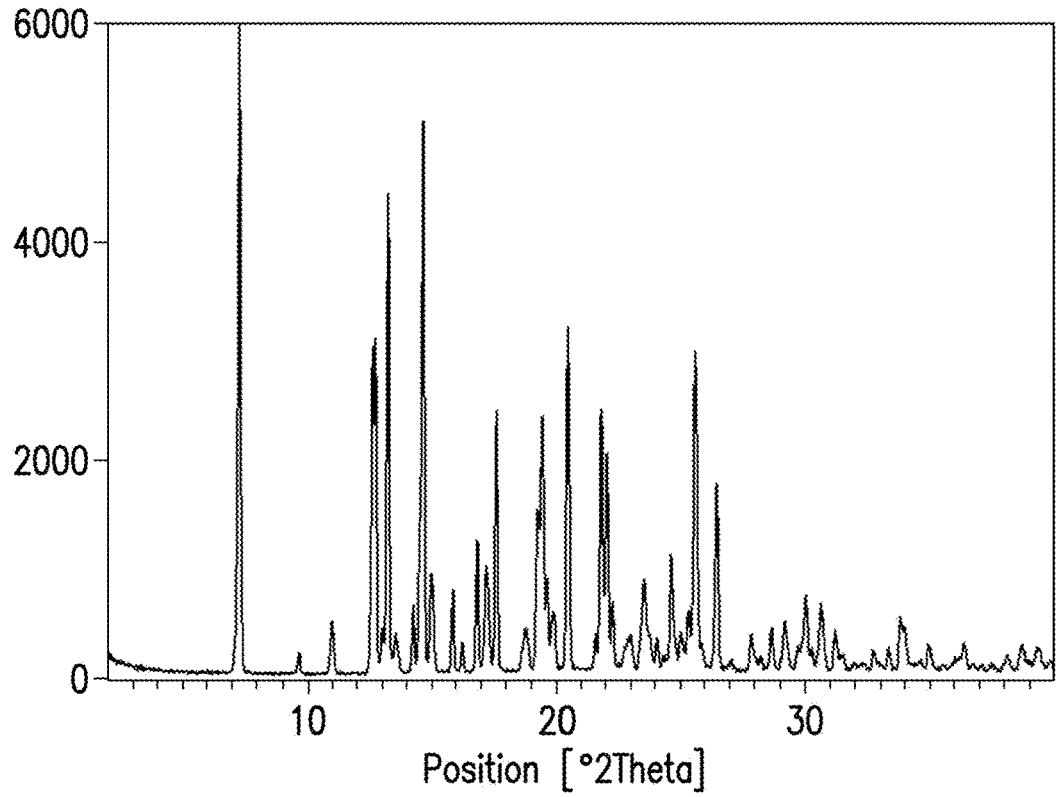
FIG. 10. An XRPD pattern of Compound A citrate hydrated methanol solvate 1.

In another embodiment, Compound A citrate hydrated methanol solvate 1 can be prepared by adding excess amount of Compound A citrate form 1 into methanol:water 3:1 (v/v) in a closed vessel to form a suspension. The suspension is stirred at RT until the completion of form transition. The crystals of Compound A citrate hydrated methanol solvate 1 can be collected by filtration and measured immediately by XRPD to prevent desolvation. An XRPD pattern of Compound A citrate hydrated methanol solvate 1 is shown in FIG. 10.

Figure 11:
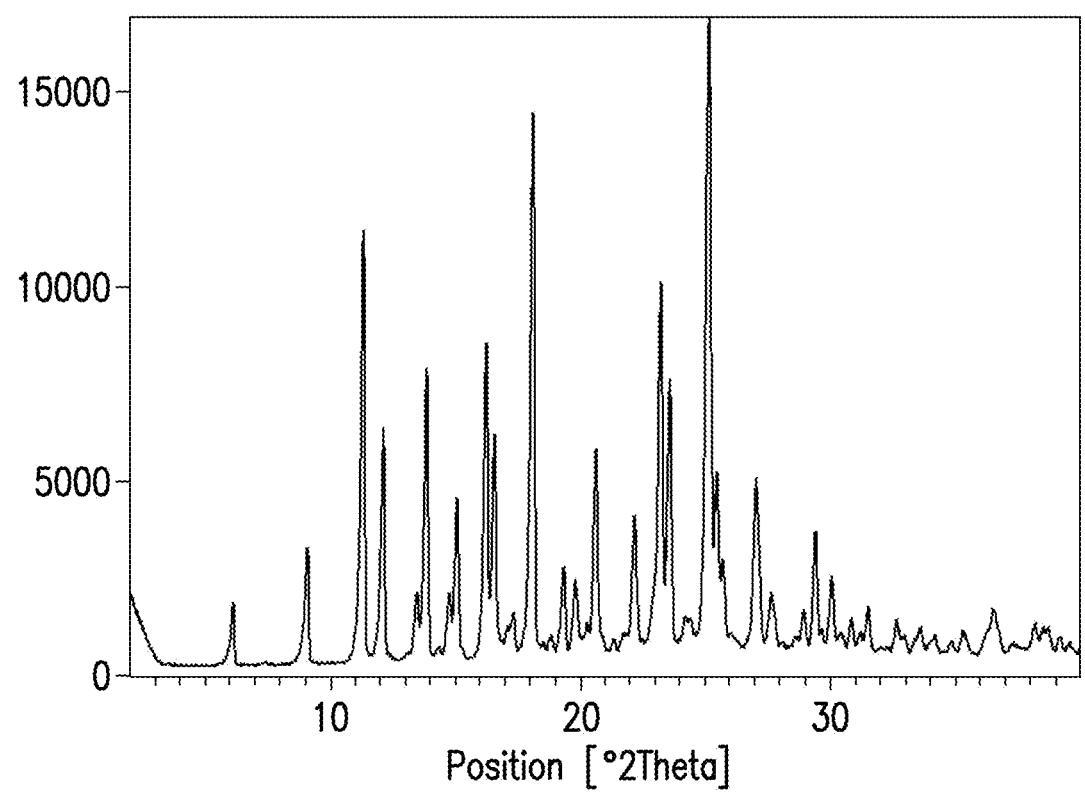
FIG. 11. An XRPD pattern of Compound A glycolate form 1.

In another embodiment, anhydrous Compound A glycolate form 1 can be prepared by adding an excess amount of Compound A free base form 1 and 4-5 eq. of glycolic acid into methanol:IPA 3:1 (v/v) in a closed vessel to form a suspension. The suspension is stirred at 50° C. until the completion of form transition. The crystals of Compound A glycolate form 1 can be collected by filtration at 50° C., washed with hot IPA at 50° C., and vacuum dried at 50° C. An XRPD pattern of Compound A glycolate form 1 is shown in FIG. 11.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A process for preparing Compound A free base of the following formula:

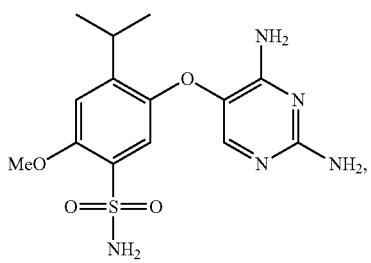

comprising a step of converting 2-isopropylphenol to 4-bromo-2-isopropylphenol hemi-DABCO co-crystal as shown below:

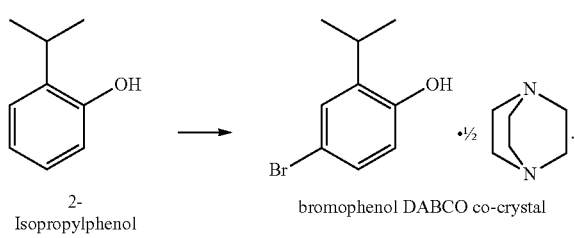

2-Isopropylphenol → bromophenol DABCO co-crystal

2. The process of claim 1, wherein the conversion to the 4-bromo-2-isopropylphenol hemi-DABCO co-crystal is carried out in the presence of NBS and MSA.

3. The process of claim 1, further comprising a step of converting the 4-bromo-2-isopropylphenol hemi-DABCO co-crystal to the methoxy phenol compound, 2-isopropyl-4-methxoy phenol, as shown below:

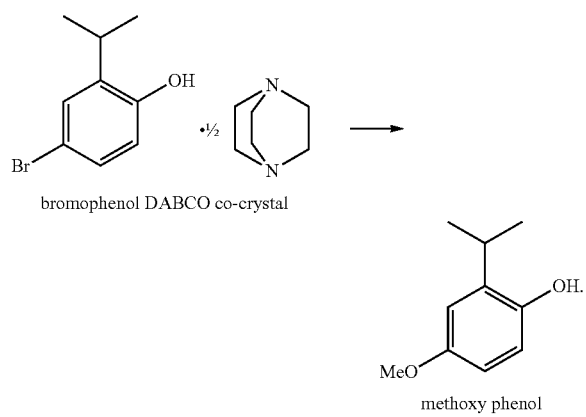

bromophenol DABCO co-crystal → methoxy phenol

4. The process of claim 3, wherein the conversion to the 2-isopropyl-4-methxoy phenol is carried out in the presence of NaOMe and with CuBr as a catalyst.

5. The process of claim 4, wherein the conversion is carried out in the presence of MeOH and DMF.

6. The process of claim 3, further comprising a step of reacting the 2-isopropyl-4-methxoy phenol with ClCH$_2$CN to form the cyanoether compound, 2-(2-isopropyl-4-methoxyphenoxy)acetonitrile, as shown below:

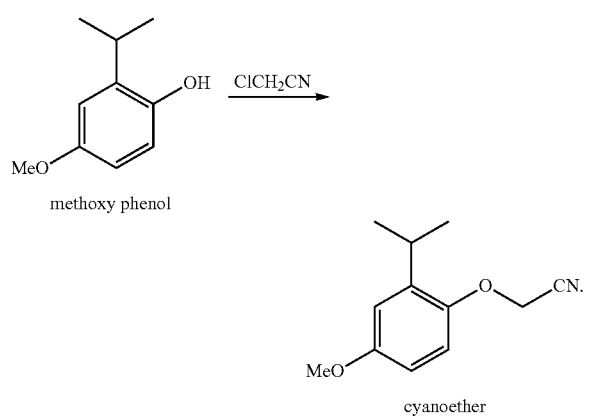

methoxy phenol → cyanoether

7. The process of claim 6, wherein the reaction to form the cyanoether compound is carried out at a temperature from about 20° C. to about 60° C.

8. The process of claim 6, further comprising a step of converting the cyanoether compound, 2-(2-isopropyl-4-methoxyphenoxy)acetonitrile, to the diaminopyrimidine compound, 5-(2-isopropyl-4-methoxyphenoxy)pyrimidine-2,4-diamine:

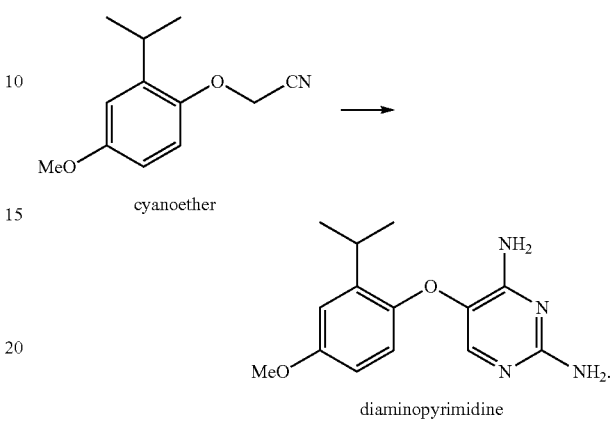

cyanoether → diaminopyrimidine

9. The process of claim 8, wherein the conversion to 5-(2-isopropyl-4-methoxyphenoxy)pyrimidine-2,4-diamine is carried out in the presence of potassium tert-butoxide in NMP and the cyanoether compound is in a solution in ethyl formate and toluene.

10. The process of claim 9, wherein the conversion to 5-(2-isopropyl-4-methoxyphenoxy)pyrimidine-2,4-diamine is carried out further in the presence of guanidine hydrochloride.

11. The process of claim 8, further comprising a step of reacting the 5-(2-isopropyl-4-methoxyphenoxy)pyrimidine-2,4-diamine with ClSO$_3$H followed by NH$_4$OH to form Compound A free base, 5-((2,4-diaminopyrimidin-5-yl)oxy)-4-isopropyl-2-methoxybenzenesulfonamide, as shown below:

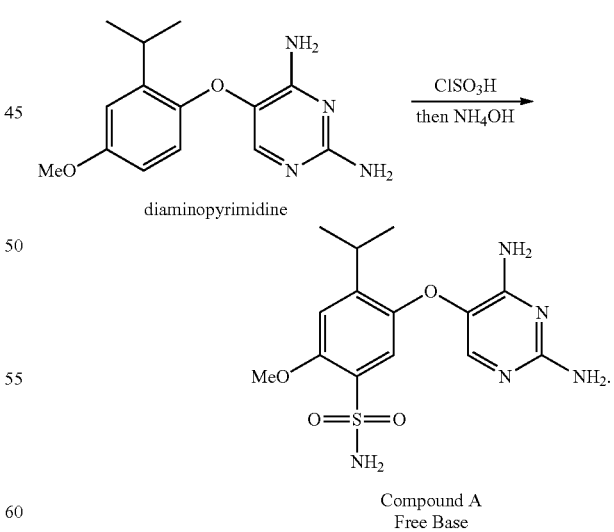

diaminopyrimidine → Compound A Free Base

12. The process of claim 11, wherein the reaction between 5-(2-isopropyl-4-methoxyphenoxy)pyrimidine-2,4-diamine and ClSO$_3$H is carried out in the presence of MeCN.

13. A process for preparing Compound A free base comprising the following steps:

(a) converting 2-isopropylphenol to 4-bromo-2-isopropylphenol hemi-DABCO co-crystal:

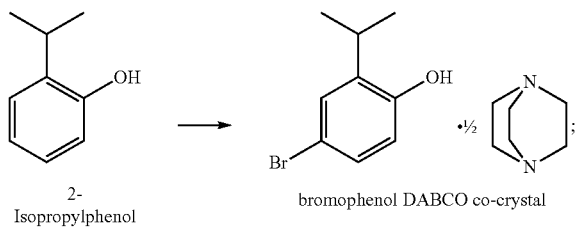

(b) converting the 4-bromo-2-isopropylphenol hemi-DABCO co-crystal to 2-isopropyl-4-methxoy phenol shown below in the presence of NaOMe:

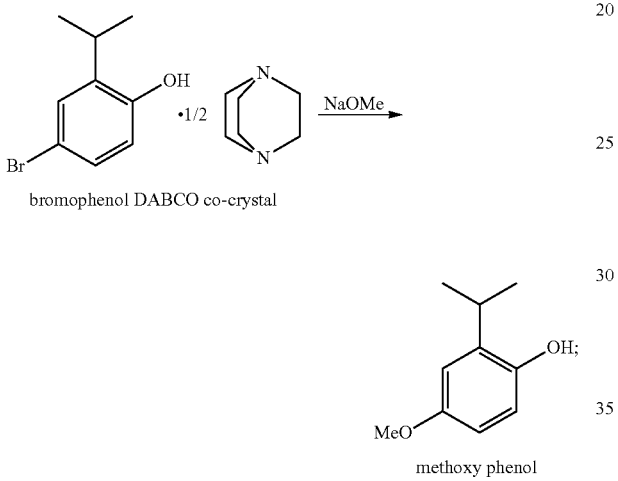

(c) reacting the 2-isopropyl-4-methxoy phenol with ClCH$_2$CN to form the cyanoether compound, 2-(2-isopropyl-4-methoxyphenoxy)acetonitrile:

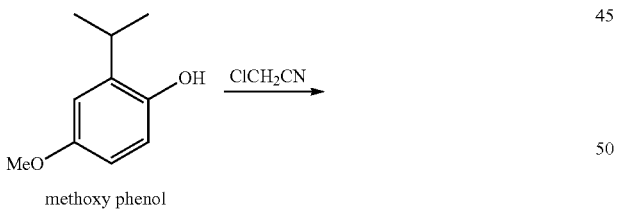

(d) converting the 2-(2-isopropyl-4-methoxyphenoxy)acetonitrile to 5-(2-isopropyl-4-methoxyphenoxy)pyrimidine-2,4-diamine:

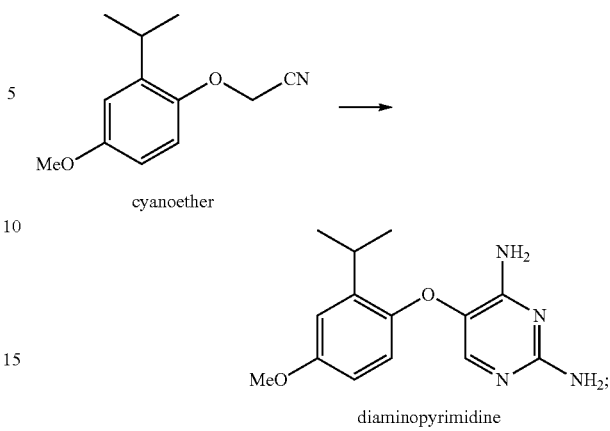

and (e) reacting 5-(2-isopropyl-4-methoxyphenoxy)pyrimidine-2,4-diamine with ClSO$_3$H followed by NH$_4$OH to form Compound A free base, 5-((2,4-diaminopyrimidin-5-yl)oxy)-4-isopropyl-2-methoxybenzenesulfonamide:

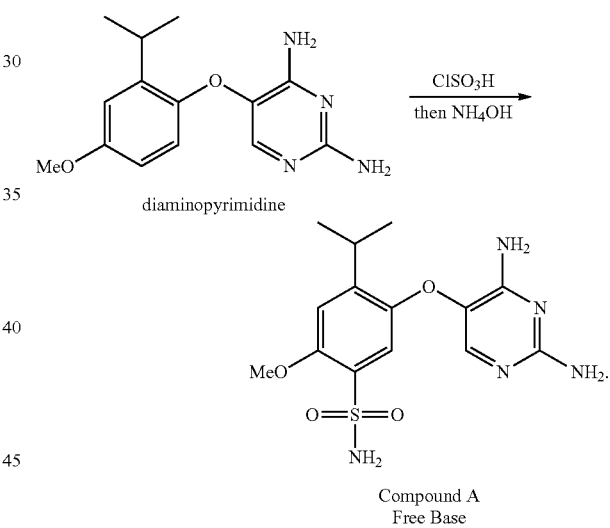

14. The process of claim 13, further comprising converting the Compound A free base to Compound A citrate salt in the presence of glycolic acid and MeOH:

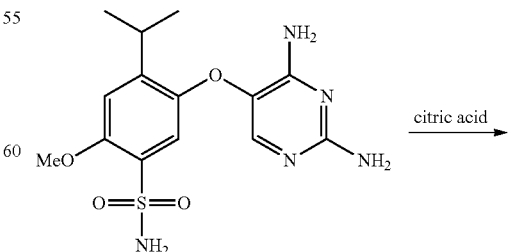

-continued

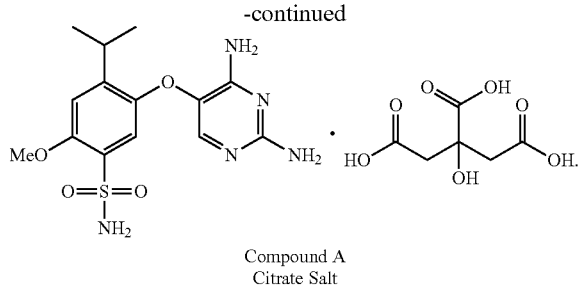

Compound A
Citrate Salt

15. The process of claim 14, wherein the overall yield from 2-isopropylphenol to Compound A citrate salt is greater than 50%.

16. Crystalline Compound A citrate methanol solvate 1 having an XRPD pattern of FIG. 8.

17. A process for preparing 4-bromo-2-isopropylphenol hemi-DABCO co-crystal comprising a step of converting 2-isopropylphenol to 4-bromo-2-isopropylphenol hemi-DABCO co-crystal as shown below:

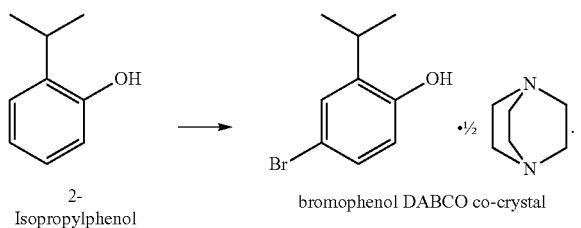

2-Isopropylphenol bromophenol DABCO co-crystal

18. The process of claim 17, wherein the conversion to the 4-bromo-2-isopropylphenol hemi-DABCO co-crystal is carried out in the presence of NBS and MSA.

19. The process of claim 17, further comprising a step of converting the 4-bromo-2-isopropylphenol hemi-DABCO co-crystal to the methoxy phenol compound, 2-isopropyl-4-methxoy phenol, as shown below:

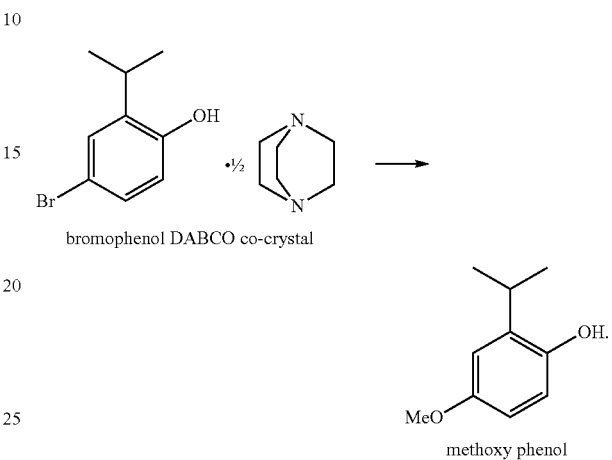

bromophenol DABCO co-crystal methoxy phenol

20. The process of claim 19, wherein the conversion to the 2-isopropyl-4-methxoy phenol is carried out in the presence of NaOMe and with CuBr as a catalyst.

* * * * *